(12) United States Patent
Pilletere et al.

(10) Patent No.: US 11,446,058 B2
(45) Date of Patent: Sep. 20, 2022

(54) FIXTURE DEVICE FOR FOLDING A SEAL MEMBER

(71) Applicant: Covidien LP, Mansfield, MA (US)

(72) Inventors: Roy J. Pilletere, North Haven, CT (US); Jason Mickus, Avon, CT (US); Matthew A. Dinino, Newington, CT (US); Eric Brown, Madison, CT (US); Nicolette R. LaPierre, Windsor Locks, CT (US); Jacob C. Baril, Norwalk, CT (US); Justin Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 349 days.

(21) Appl. No.: 16/832,069

(22) Filed: Mar. 27, 2020

(65) Prior Publication Data

US 2021/0298787 A1    Sep. 30, 2021

(51) Int. Cl.
| | |
|---|---|
| *A61B 17/34* | (2006.01) |
| *B29C 53/02* | (2006.01) |
| *A61B 17/00* | (2006.01) |
| *B29L 31/26* | (2006.01) |
| *B29L 31/00* | (2006.01) |
| *B30B 9/00* | (2006.01) |

(52) U.S. Cl.
CPC ...... *A61B 17/3462* (2013.01); *A61B 17/3423* (2013.01); *B29C 53/02* (2013.01); *A61B 2017/00526* (2013.01); *A61B 2017/3464* (2013.01); *B29L 2031/26* (2013.01); *B29L 2031/7546* (2013.01); *B30B 9/00* (2013.01)

(58) Field of Classification Search
CPC ..................... A61B 17/3462; A61B 17/3423
See application file for complete search history.

(56) References Cited

U.S. PATENT DOCUMENTS

| | | | |
|---|---|---|---|
| 3,402,710 A | | 9/1968 | Paleschuck |
| 3,495,586 A | * | 2/1970 | Regenbogen ............ A61B 1/31 600/101 |
| 4,016,884 A | | 4/1977 | Kwan-Gett |
| (Continued) | | | |

FOREIGN PATENT DOCUMENTS

| | | |
|---|---|---|
| CA | 2702419 A1 | 11/2010 |
| CN | 202313634 U | 7/2012 |
| (Continued) | | |

OTHER PUBLICATIONS

European Search Report dated Jul. 26, 2021, corresponding to counterpart European Application No. 21165312.6; 5 pages.

*Primary Examiner* — Christian A Sevilla
(74) *Attorney, Agent, or Firm* — Carter, DeLuca & Farrell LLP

(57) ABSTRACT

A fixation device for folding a seal member includes a frame having a horizontal portion and an upright portion, a press assembly secured to the upright portion of the frame, and a nest assembly secured to the horizontal portion of the frame. The press assembly includes a handle assembly and an anvil assembly operably connected to the handle assembly. The nest assembly includes a clamping assembly, a folding assembly supported on the clamping assembly, a support assembly supported on the folding assembly, and a nest member. The support assembly includes a support plate and a seal clamp for securing a seal member.

18 Claims, 12 Drawing Sheets

(56) References Cited

U.S. PATENT DOCUMENTS

| | | |
|---|---|---|
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,619,643 A | 10/1986 | Bai |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,741 A | 5/1993 | Spaeth |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,271,380 A | 12/1993 | Riek et al. |
| 5,290,245 A | 3/1994 | Dennis |
| 5,290,249 A | 3/1994 | Foster et al. |
| 5,308,336 A | 5/1994 | Hart et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,334,150 A | 8/1994 | Kaali |
| 5,336,169 A | 8/1994 | Divilio et al. |
| 5,336,203 A | 8/1994 | Goldhardt et al. |
| 5,337,937 A | 8/1994 | Remiszewski et al. |
| 5,345,927 A | 9/1994 | Bonutti |
| 5,346,459 A | 9/1994 | Allen |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,380,291 A | 1/1995 | Kaali |
| 5,385,552 A | 1/1995 | Haber et al. |
| 5,385,553 A | 1/1995 | Hart et al. |
| 5,391,156 A | 2/1995 | Hildwein et al. |
| 5,394,863 A | 3/1995 | Sanford et al. |
| 5,395,367 A | 3/1995 | Wilk |
| 5,407,433 A | 4/1995 | Loomas |
| 5,431,151 A | 7/1995 | Riek et al. |
| 5,437,683 A | 8/1995 | Neumann et al. |
| 5,445,615 A | 8/1995 | Yoon |
| 5,451,222 A | 9/1995 | De Maagd et al. |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,610 A | 5/1996 | Giglio et al. |
| 5,520,698 A | 5/1996 | Koh |
| 5,522,791 A | 6/1996 | Leyva |
| 5,524,501 A | 6/1996 | Patterson et al. |
| 5,524,644 A | 6/1996 | Crook |
| 5,538,509 A | 7/1996 | Dunlap et al. |
| 5,540,648 A | 7/1996 | Yoon |
| 5,545,150 A | 8/1996 | Danks et al. |
| 5,545,179 A | 8/1996 | Williamson, IV |
| 5,549,565 A | 8/1996 | Ryan et al. |
| 5,551,947 A | 9/1996 | Kaali |
| 5,556,385 A | 9/1996 | Andersen |
| 5,569,159 A | 10/1996 | Anderson et al. |
| 5,569,205 A | 10/1996 | Hart et al. |
| 5,569,291 A | 10/1996 | Privitera et al. |
| 5,569,292 A | 10/1996 | Scwemberger et al. |
| 5,577,993 A | 11/1996 | Zhu et al. |
| 5,591,192 A | 1/1997 | Privitera et al. |
| 5,601,581 A | 2/1997 | Fogarty et al. |
| 5,609,562 A | 3/1997 | Kaali |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | de la Torre et al. |
| 5,656,013 A | 8/1997 | Yoon |
| 5,672,168 A | 9/1997 | de la Torre et al. |
| 5,683,378 A | 11/1997 | Christy |
| 5,685,820 A | 11/1997 | Riek et al. |
| 5,685,857 A | 11/1997 | Negus et al. |
| 5,685,862 A | 11/1997 | Mahurkar |
| 5,697,946 A | 12/1997 | Hopper et al. |
| 5,709,671 A | 1/1998 | Stephens et al. |
| 5,709,675 A | 1/1998 | Williams |
| 5,713,858 A | 2/1998 | Heruth et al. |
| 5,713,869 A | 2/1998 | Morejon |
| 5,720,730 A | 2/1998 | Blake, III |
| 5,720,761 A | 2/1998 | Kaali |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,752,970 A | 5/1998 | Yoon |
| 5,776,112 A | 7/1998 | Stephens et al. |
| 5,782,817 A | 7/1998 | Franzel et al. |
| 5,792,113 A | 8/1998 | Kramer et al. |
| 5,795,290 A | 8/1998 | Bridges |
| 5,800,451 A | 9/1998 | Buess et al. |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,471 A | 2/1999 | Ryan et al. |
| 5,871,474 A | 2/1999 | Hermann et al. |
| 5,876,413 A | 3/1999 | Fogarty et al. |
| 5,893,875 A | 4/1999 | O'Connor et al. |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,007,481 A | 12/1999 | Riek et al. |
| 6,017,355 A | 1/2000 | Hessel et al. |
| 6,018,094 A | 1/2000 | Fox |
| 6,024,736 A | 2/2000 | de la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |

(56) References Cited

U.S. PATENT DOCUMENTS

| | | |
|---|---|---|
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,093,176 A | 7/2000 | Dennis |
| 6,099,505 A | 8/2000 | Ryan et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,171,282 B1 | 1/2001 | Ragsdale |
| 6,197,002 B1 | 3/2001 | Peterson |
| 6,213,957 B1 | 4/2001 | Milliman et al. |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | de la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | de la Torre et al. |
| 6,319,246 B1 | 11/2001 | de la Torre et al. |
| 6,328,720 B1 | 12/2001 | McNally et al. |
| 6,329,637 B1 | 12/2001 | Hembree et al. |
| 6,355,028 B2 | 3/2002 | Castaneda et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,478,806 B2 | 11/2002 | McFarlane |
| 6,485,410 B1 | 11/2002 | Loy |
| 6,485,467 B1 | 11/2002 | Crook et al. |
| 6,487,806 B2 | 12/2002 | Murello et al. |
| 6,488,620 B1 | 12/2002 | Segermark et al. |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,551,282 B1 | 4/2003 | Exline et al. |
| 6,558,371 B2 | 5/2003 | Dorn |
| 6,562,022 B2 | 5/2003 | Hoste et al. |
| 6,569,120 B1 | 5/2003 | Green et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,038 B2 | 9/2003 | Bonutti et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,684,405 B2 | 2/2004 | Lezdey |
| 6,702,787 B2 | 3/2004 | Racenet et al. |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,736,797 B1 | 5/2004 | Larsen et al. |
| 6,740,064 B1 | 5/2004 | Sorrentino et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,835,201 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,855,128 B2 | 2/2005 | Swenson |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,942,671 B1 | 9/2005 | Smith |
| 6,945,932 B1 | 9/2005 | Caldwell et al. |
| 6,958,037 B2 | 10/2005 | Ewers et al. |
| 6,960,164 B2 | 11/2005 | O'Heeron |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 * | 5/2006 | Taylor ............... A61B 17/3423 600/114 |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,300,448 B2 | 11/2007 | Criscuolo et al. |
| 7,316,699 B2 | 1/2008 | McFarlane |
| 7,320,694 B2 | 1/2008 | O'Heeron |
| 7,331,940 B2 | 2/2008 | Sommerich |
| 7,344,547 B2 | 3/2008 | Piskun |
| 7,370,694 B2 | 5/2008 | Shimizu et al. |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,494,481 B2 | 2/2009 | Moberg et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |

(56) References Cited

U.S. PATENT DOCUMENTS

| | | | |
|---|---|---|---|
| 7,537,564 B2 * | 5/2009 | Bonadio | A61B 17/0293 600/208 |
| 7,540,839 B2 | 6/2009 | Butler et al. | |
| 7,559,893 B2 | 7/2009 | Bonadio et al. | |
| 7,608,082 B2 | 10/2009 | Cuevas et al. | |
| 7,625,361 B2 | 12/2009 | Suzuki et al. | |
| 7,645,232 B2 | 1/2010 | Shluzas | |
| 7,650,887 B2 | 1/2010 | Nguyen et al. | |
| 7,678,046 B2 | 3/2010 | White et al. | |
| 7,686,823 B2 | 3/2010 | Pingleton et al. | |
| 7,704,207 B2 | 4/2010 | Albrecht et al. | |
| 7,708,713 B2 | 5/2010 | Albrecht et al. | |
| 7,717,846 B2 | 5/2010 | Zirps et al. | |
| 7,717,847 B2 | 5/2010 | Smith | |
| 7,721,742 B2 | 5/2010 | Kalloo et al. | |
| 7,727,146 B2 | 6/2010 | Albrecht et al. | |
| 7,730,629 B2 | 6/2010 | Kim | |
| 7,736,306 B2 | 6/2010 | Brustad et al. | |
| 7,744,569 B2 | 6/2010 | Smith | |
| 7,753,901 B2 | 7/2010 | Piskun et al. | |
| 7,758,500 B2 | 7/2010 | Boyd et al. | |
| 7,758,603 B2 | 7/2010 | Taylor et al. | |
| 7,762,995 B2 | 7/2010 | Eversull et al. | |
| 7,766,824 B2 | 8/2010 | Jensen et al. | |
| 7,787,963 B2 | 8/2010 | Geistert et al. | |
| 7,794,644 B2 | 9/2010 | Taylor et al. | |
| 7,798,998 B2 | 9/2010 | Thompson et al. | |
| 7,811,251 B2 | 10/2010 | Wenchell et al. | |
| 7,815,567 B2 | 10/2010 | Albrecht et al. | |
| 7,837,612 B2 | 11/2010 | Gill et al. | |
| 7,846,123 B2 | 12/2010 | Vassiliades et al. | |
| 7,850,600 B1 | 12/2010 | Piskun | |
| 7,850,655 B2 | 12/2010 | Pasqualucci | |
| 7,850,667 B2 | 12/2010 | Gresham | |
| 7,867,164 B2 | 1/2011 | Butler et al. | |
| 7,896,889 B2 | 3/2011 | Mazzocchi et al. | |
| 7,905,829 B2 | 3/2011 | Nishimura et al. | |
| 7,909,760 B2 | 3/2011 | Albrecht et al. | |
| 7,913,697 B2 | 3/2011 | Nguyen et al. | |
| 7,918,827 B2 | 4/2011 | Smith | |
| 7,947,058 B2 | 5/2011 | Kahle et al. | |
| 7,951,076 B2 | 5/2011 | Hart et al. | |
| 7,955,257 B2 | 6/2011 | Frasier et al. | |
| 7,955,313 B2 | 6/2011 | Boismier | |
| 7,985,232 B2 | 7/2011 | Potter et al. | |
| 7,998,068 B2 | 8/2011 | Bonadio et al. | |
| 8,002,750 B2 | 8/2011 | Smith | |
| 8,002,786 B2 | 8/2011 | Beckman et al. | |
| 8,012,128 B2 | 9/2011 | Franer et al. | |
| 8,021,296 B2 | 9/2011 | Bonadio et al. | |
| 8,025,670 B2 | 9/2011 | Sharp et al. | |
| 8,029,475 B2 | 10/2011 | Franer et al. | |
| 8,038,652 B2 | 10/2011 | Morrison et al. | |
| 8,052,653 B2 | 11/2011 | Gratwohl et al. | |
| 8,066,673 B2 | 11/2011 | Hart et al. | |
| 8,079,986 B2 | 12/2011 | Taylor et al. | |
| 8,092,430 B2 | 1/2012 | Richard et al. | |
| 8,092,431 B2 | 1/2012 | Lunn et al. | |
| 8,105,234 B2 | 1/2012 | Ewers et al. | |
| 8,109,873 B2 | 2/2012 | Albrecht et al. | |
| 8,118,735 B2 | 2/2012 | Voegele | |
| 8,128,590 B2 | 3/2012 | Albrecht et al. | |
| 8,137,318 B2 | 3/2012 | Schweitzer et al. | |
| 8,147,453 B2 | 4/2012 | Albrecht et al. | |
| 8,152,828 B2 | 4/2012 | Taylor et al. | |
| 8,157,786 B2 | 4/2012 | Miller et al. | |
| 8,157,817 B2 | 4/2012 | Bonadio et al. | |
| 8,187,177 B2 | 5/2012 | Kahle et al. | |
| 8,187,178 B2 | 5/2012 | Bonadio et al. | |
| 8,206,411 B2 | 6/2012 | Thompson et al. | |
| 8,241,209 B2 | 8/2012 | Shelton, IV et al. | |
| 8,262,568 B2 | 9/2012 | Albrecht et al. | |
| 8,267,952 B2 | 9/2012 | Kahle et al. | |
| 8,323,184 B2 | 12/2012 | Spiegal et al. | |
| 8,335,783 B2 | 12/2012 | Milby | |
| 8,343,047 B2 | 1/2013 | Albrecht et al. | |
| 8,353,824 B2 | 1/2013 | Shelton, IV et al. | |
| 8,398,666 B2 | 3/2013 | McFarlane | |
| 8,403,889 B2 | 3/2013 | Richard | |
| 8,480,683 B2 | 7/2013 | Fowler et al. | |
| 8,574,153 B2 | 11/2013 | Richard | |
| 8,585,632 B2 | 11/2013 | Okoniewski | |
| 8,597,180 B2 | 12/2013 | Copeland et al. | |
| 8,961,406 B2 | 2/2015 | Ortiz et al. | |
| 10,022,149 B2 | 7/2018 | Holsten et al. | |
| 10,568,660 B2 | 2/2020 | Zhou | |
| 10,653,449 B2 | 5/2020 | Main et al. | |
| 2001/0018591 A1 * | 8/2001 | Brock | G16H 20/40 606/130 |
| 2001/0037053 A1 | 11/2001 | Bonadio et al. | |
| 2002/0042605 A1 * | 4/2002 | Castaneda | A61B 17/3417 606/1 |
| 2002/0055714 A1 | 5/2002 | Rothschild | |
| 2002/0091410 A1 | 7/2002 | Ben-David et al. | |
| 2002/0173748 A1 | 11/2002 | McConnell et al. | |
| 2003/0014076 A1 | 1/2003 | Mollenauer et al. | |
| 2003/0093104 A1 | 5/2003 | Bonner et al. | |
| 2003/0109853 A1 | 6/2003 | Harding et al. | |
| 2003/0187376 A1 | 10/2003 | Rambo | |
| 2003/0187397 A1 | 10/2003 | Vitali | |
| 2003/0233115 A1 | 12/2003 | Eversull et al. | |
| 2003/0236549 A1 | 12/2003 | Bonadio et al. | |
| 2004/0006356 A1 | 1/2004 | Smith | |
| 2004/0054353 A1 | 3/2004 | Taylor | |
| 2004/0059297 A1 | 3/2004 | Racenet et al. | |
| 2004/0073090 A1 | 4/2004 | Butler et al. | |
| 2004/0092795 A1 | 5/2004 | Bonadio et al. | |
| 2004/0102804 A1 | 5/2004 | Chin | |
| 2004/0111061 A1 | 6/2004 | Curran | |
| 2004/0138529 A1 | 7/2004 | Wiltshire et al. | |
| 2004/0138676 A1 * | 7/2004 | Crabtree | A61B 17/3403 606/108 |
| 2004/0186434 A1 | 9/2004 | Harding et al. | |
| 2004/0204682 A1 | 10/2004 | Smith | |
| 2004/0204734 A1 | 10/2004 | Wagner et al. | |
| 2004/0215209 A1 | 10/2004 | Almond et al. | |
| 2004/0267096 A1 | 12/2004 | Caldwell et al. | |
| 2004/0267204 A1 | 12/2004 | Brustowicz | |
| 2005/0010238 A1 | 1/2005 | Potter et al. | |
| 2005/0020884 A1 | 1/2005 | Hart et al. | |
| 2005/0033342 A1 | 2/2005 | Hart et al. | |
| 2005/0070850 A1 | 3/2005 | Albrecht | |
| 2005/0070851 A1 | 3/2005 | Thompson et al. | |
| 2005/0070935 A1 | 3/2005 | Ortiz | |
| 2005/0070946 A1 | 3/2005 | Franer et al. | |
| 2005/0070947 A1 | 3/2005 | Franer et al. | |
| 2005/0096695 A1 | 5/2005 | Olich | |
| 2005/0119525 A1 | 6/2005 | Takemoto | |
| 2005/0137459 A1 | 6/2005 | Chin et al. | |
| 2005/0148823 A1 | 7/2005 | Vaugh et al. | |
| 2005/0192483 A1 | 9/2005 | Bonadio et al. | |
| 2005/0192594 A1 | 9/2005 | Skakoon et al. | |
| 2005/0203346 A1 | 9/2005 | Bonadio et al. | |
| 2005/0209608 A1 | 9/2005 | O'Heeron | |
| 2005/0212221 A1 | 9/2005 | Smith et al. | |
| 2005/0222582 A1 | 10/2005 | Wenchell | |
| 2005/0245876 A1 | 11/2005 | Khosravi et al. | |
| 2005/0251092 A1 | 11/2005 | Howell et al. | |
| 2005/0251190 A1 | 11/2005 | McFarlane | |
| 2005/0277946 A1 | 12/2005 | Greenhalgh | |
| 2006/0020281 A1 | 1/2006 | Smith | |
| 2006/0071432 A1 | 4/2006 | Staudner | |
| 2006/0129165 A1 | 6/2006 | Edoga et al. | |
| 2006/0149137 A1 | 7/2006 | Pingleton et al. | |
| 2006/0149306 A1 | 7/2006 | Hart et al. | |
| 2006/0161049 A1 | 7/2006 | Beane et al. | |
| 2006/0161050 A1 | 7/2006 | Butler et al. | |
| 2006/0211992 A1 | 9/2006 | Prosek | |
| 2006/0212063 A1 | 9/2006 | Wilk | |
| 2006/0217665 A1 | 9/2006 | Prosek | |
| 2006/0224161 A1 | 10/2006 | Bhattacharyya | |
| 2006/0241651 A1 | 10/2006 | Wilk | |
| 2006/0247498 A1 | 11/2006 | Bonadio et al. | |
| 2006/0247499 A1 | 11/2006 | Butler et al. | |

(56) References Cited

U.S. PATENT DOCUMENTS

| | | |
|---|---|---|
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0270911 A1 | 11/2006 | Voegele et al. |
| 2006/0276751 A1 | 12/2006 | Haberland et al. |
| 2007/0088277 A1 | 4/2007 | McGinley et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0185453 A1 | 8/2007 | Michael et al. |
| 2007/0203398 A1 | 8/2007 | Bonadio et al. |
| 2007/0208312 A1 | 9/2007 | Norton et al. |
| 2007/0225650 A1 | 9/2007 | Hart et al. |
| 2007/0239108 A1 | 10/2007 | Albrecht et al. |
| 2007/0255218 A1 | 11/2007 | Franer |
| 2007/0270654 A1 | 11/2007 | Pignato et al. |
| 2007/0270882 A1 | 11/2007 | Hjelle et al. |
| 2008/0009826 A1 | 1/2008 | Miller et al. |
| 2008/0021360 A1 | 1/2008 | Fihe et al. |
| 2008/0027476 A1 | 1/2008 | Piskun |
| 2008/0048011 A1 | 2/2008 | Weller |
| 2008/0051739 A1 | 2/2008 | McFarlane |
| 2008/0058723 A1 | 3/2008 | Lipchitz et al. |
| 2008/0091143 A1 | 4/2008 | Taylor et al. |
| 2008/0097162 A1 | 4/2008 | Bonadio et al. |
| 2008/0097332 A1 | 4/2008 | Greenhalgh et al. |
| 2008/0119868 A1 | 5/2008 | Sharp et al. |
| 2008/0125794 A1* | 5/2008 | Brock .............. A61B 34/35 606/130 |
| 2008/0146884 A1 | 6/2008 | Beckman et al. |
| 2008/0161758 A1 | 7/2008 | Insignares |
| 2008/0161826 A1 | 7/2008 | Guiraudon |
| 2008/0177265 A1 | 7/2008 | Lechot |
| 2008/0188868 A1 | 8/2008 | Weitzner et al. |
| 2008/0194973 A1 | 8/2008 | Imam |
| 2008/0200767 A1 | 8/2008 | Ewers et al. |
| 2008/0208222 A1 | 8/2008 | Beckman et al. |
| 2008/0249475 A1 | 10/2008 | Albrecht et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036738 A1 | 2/2009 | Cuschieri et al. |
| 2009/0036745 A1 | 2/2009 | Bonadio et al. |
| 2009/0093752 A1 | 4/2009 | Richard et al. |
| 2009/0093835 A1 | 4/2009 | Heinrich et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0221968 A1 | 9/2009 | Morrison et al. |
| 2009/0227843 A1 | 9/2009 | Smith et al. |
| 2009/0234293 A1 | 9/2009 | Albrecht et al. |
| 2009/0275880 A1 | 11/2009 | Pasqualucci |
| 2009/0326330 A1 | 12/2009 | Bonadio et al. |
| 2009/0326332 A1 | 12/2009 | Carter |
| 2010/0016800 A1 | 1/2010 | Rockrohr |
| 2010/0030155 A1 | 2/2010 | Gyrn et al. |
| 2010/0049138 A1 | 2/2010 | Smith et al. |
| 2010/0063450 A1 | 3/2010 | Smith et al. |
| 2010/0063452 A1 | 3/2010 | Edelman et al. |
| 2010/0100043 A1 | 4/2010 | Racenet |
| 2010/0113886 A1 | 5/2010 | Piskun et al. |
| 2010/0222801 A1 | 9/2010 | Pingleton et al. |
| 2010/0228090 A1 | 9/2010 | Weisenburgh, II |
| 2010/0228094 A1 | 9/2010 | Ortiz et al. |
| 2010/0228096 A1 | 9/2010 | Weisenburgh, II et al. |
| 2010/0240960 A1 | 9/2010 | Richard |
| 2010/0249516 A1 | 9/2010 | Shelton, IV et al. |
| 2010/0249523 A1 | 9/2010 | Spiegal et al. |
| 2010/0249524 A1 | 9/2010 | Ransden et al. |
| 2010/0261975 A1 | 10/2010 | Huey et al. |
| 2010/0262080 A1 | 10/2010 | Shelton, IV et al. |
| 2010/0280326 A1 | 11/2010 | Hess et al. |
| 2010/0286484 A1 | 11/2010 | Stellon et al. |
| 2010/0286506 A1 | 11/2010 | Ransden et al. |
| 2010/0286706 A1 | 11/2010 | Judson |
| 2010/0298646 A1 | 11/2010 | Stellon et al. |
| 2010/0312063 A1 | 12/2010 | Hess et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0054260 A1 | 3/2011 | Albrecht et al. |
| 2011/0082341 A1 | 4/2011 | Man et al. |
| 2011/0082343 A1 | 4/2011 | Okoniewski |
| 2011/0082346 A1 | 4/2011 | Stopek |
| 2011/0087159 A1 | 4/2011 | Parihar et al. |
| 2011/0087168 A1 | 4/2011 | Parihar et al. |
| 2011/0087169 A1 | 4/2011 | Parihar et al. |
| 2011/0118553 A1 | 5/2011 | Stopek |
| 2011/0118833 A1 | 5/2011 | Reichenbach et al. |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |
| 2011/0190592 A1 | 8/2011 | Kahle et al. |
| 2011/0201891 A1 | 8/2011 | Smith et al. |
| 2011/0251463 A1 | 10/2011 | Kleyman |
| 2011/0251464 A1 | 10/2011 | Kleyman |
| 2011/0251465 A1 | 10/2011 | Kleyman |
| 2011/0251466 A1 | 10/2011 | Kleyman et al. |
| 2011/0251559 A1 | 10/2011 | Tal et al. |
| 2011/0251560 A1 | 10/2011 | Albrecht et al. |
| 2011/0251633 A1 | 10/2011 | Smith |
| 2011/0276002 A1 | 11/2011 | Bierman |
| 2011/0313250 A1 | 12/2011 | Kleyman |
| 2012/0010569 A1 | 1/2012 | Parihar |
| 2012/0041371 A1 | 2/2012 | Tal et al. |
| 2012/0059640 A1 | 3/2012 | Roy et al. |
| 2012/0065590 A1 | 3/2012 | Bierman et al. |
| 2012/0109064 A1 | 5/2012 | Fischvogt et al. |
| 2012/0130177 A1 | 5/2012 | Davis |
| 2012/0130181 A1 | 5/2012 | Davis |
| 2012/0130182 A1 | 5/2012 | Rodrigues, Jr. et al. |
| 2012/0130183 A1 | 5/2012 | Barnes |
| 2012/0130184 A1 | 5/2012 | Richard |
| 2012/0130185 A1 | 5/2012 | Pribanic |
| 2012/0130186 A1 | 5/2012 | Stopek et al. |
| 2012/0130187 A1 | 5/2012 | Okoniewski |
| 2012/0130188 A1 | 5/2012 | Okoniewski |
| 2012/0130190 A1 | 5/2012 | Kasvikis |
| 2012/0130191 A1 | 5/2012 | Pribanic |
| 2012/0149987 A1 | 6/2012 | Richard et al. |
| 2012/0157777 A1 | 6/2012 | Okoniewski |
| 2012/0157779 A1 | 6/2012 | Fischvogt |
| 2012/0157780 A1 | 6/2012 | Okoniewski et al. |
| 2012/0157781 A1 | 6/2012 | Kleyman |
| 2012/0157782 A1 | 6/2012 | Alfieri |
| 2012/0157783 A1 | 6/2012 | Okoniewski et al. |
| 2012/0157784 A1 | 6/2012 | Kleyman et al. |
| 2012/0157785 A1 | 6/2012 | Kleyman |
| 2012/0157786 A1 | 6/2012 | Pribanic |
| 2012/0190931 A1 | 7/2012 | Stopek |
| 2012/0190932 A1 | 7/2012 | Okoniewski |
| 2012/0190933 A1 | 7/2012 | Kleyman |
| 2012/0209077 A1 | 8/2012 | Racenet |
| 2012/0209078 A1 | 8/2012 | Pribanic et al. |
| 2012/0245427 A1 | 9/2012 | Kleyman |
| 2012/0245429 A1 | 9/2012 | Smith |
| 2012/0245430 A1 | 9/2012 | Kleyman et al. |
| 2012/0283520 A1 | 11/2012 | Kleyman |
| 2012/0316596 A1 | 12/2012 | Taylor et al. |
| 2013/0225930 A1 | 8/2013 | Smith |
| 2013/0225931 A1 | 8/2013 | Cruz et al. |
| 2013/0245373 A1 | 9/2013 | Okoniewski |

(56) References Cited

U.S. PATENT DOCUMENTS

| | | | |
|---|---|---|---|
| 2013/0274559 A1 | 10/2013 | Fowler et al. | |
| 2013/0310651 A1 | 11/2013 | Altieri | |
| 2014/0018632 A1 | 1/2014 | Kleyman | |
| 2015/0025477 A1 | 1/2015 | Evans | |
| 2015/0065808 A1 | 3/2015 | Van Wyk et al. | |
| 2015/0223833 A1 | 8/2015 | Coffeen et al. | |

FOREIGN PATENT DOCUMENTS

| | | |
|---|---|---|
| DE | 202008009527 U1 | 10/2008 |
| EP | 0226026 A2 | 6/1987 |
| EP | 0538060 A1 | 4/1993 |
| EP | 0577400 A1 | 1/1994 |
| EP | 0630660 A1 | 12/1994 |
| EP | 0807416 A2 | 11/1997 |
| EP | 0950376 A1 | 10/1999 |
| EP | 1188415 A2 | 3/2002 |
| EP | 1312318 A1 | 5/2003 |
| EP | 1774918 A1 | 4/2007 |
| EP | 1932485 A1 | 6/2008 |
| EP | 1994896 A1 | 11/2008 |
| EP | 2044889 A1 | 4/2009 |
| EP | 2044897 A1 | 4/2009 |
| EP | 2080494 A1 | 7/2009 |
| EP | 2095781 A2 | 9/2009 |
| EP | 2098182 A2 | 9/2009 |
| EP | 2138117 A1 | 12/2009 |
| EP | 2138118 A2 | 12/2009 |
| EP | 2145593 A1 | 1/2010 |
| EP | 2181657 A2 | 5/2010 |
| EP | 2226025 A1 | 9/2010 |
| EP | 2229900 A1 | 9/2010 |
| EP | 2238924 A1 | 10/2010 |
| EP | 2238925 A1 | 10/2010 |
| EP | 2238926 A2 | 10/2010 |
| EP | 2238933 A1 | 10/2010 |
| EP | 2248478 A1 | 11/2010 |
| EP | 2248482 A1 | 11/2010 |
| EP | 2253283 A1 | 11/2010 |
| EP | 2272450 A2 | 1/2011 |
| EP | 2277464 A1 | 1/2011 |
| EP | 2289438 A1 | 3/2011 |
| EP | 2292165 | 3/2011 |
| EP | 2343019 | 7/2011 |
| GB | 2469083 | 4/2009 |
| JP | 2001525693 A | 12/2001 |
| JP | 2004532660 A | 10/2004 |
| JP | 2005103285 A | 4/2005 |
| JP | 2006187603 A | 7/2006 |
| JP | 2008289889 A | 12/2008 |
| JP | 2009534124 A | 9/2009 |
| JP | 2011515128 A | 5/2011 |
| WO | 8401512 | 4/1984 |
| WO | 9314801 | 8/1993 |
| WO | 9404067 | 3/1994 |
| WO | 9610963 | 4/1996 |
| WO | 9636283 | 11/1996 |
| WO | 9733520 | 9/1997 |
| WO | 9742889 | 11/1997 |
| WO | 9850093 A1 | 11/1998 |
| WO | 9916368 | 4/1999 |
| WO | 9922804 | 5/1999 |
| WO | 9929250 | 6/1999 |
| WO | 0032116 | 6/2000 |
| WO | 0032120 | 6/2000 |
| WO | 0054675 | 9/2000 |
| WO | 0108581 | 2/2001 |
| WO | 0149363 | 7/2001 |
| WO | 0207611 | 1/2002 |
| WO | 03034908 A2 | 5/2003 |
| WO | 03071926 | 9/2003 |
| WO | 03077726 | 9/2003 |
| WO | 2004043275 | 5/2004 |
| WO | 2004054456 | 7/2004 |
| WO | 2004075741 | 9/2004 |
| WO | 2004075930 | 9/2004 |
| WO | 2005058409 | 6/2005 |
| WO | 2006019723 | 2/2006 |
| WO | 2006100658 A2 | 9/2006 |
| WO | 2006110733 | 10/2006 |
| WO | 2006118650 A1 | 11/2006 |
| WO | 2007018458 | 2/2007 |
| WO | 2007095703 | 8/2007 |
| WO | 2007143200 | 12/2007 |
| WO | 2008015566 A2 | 2/2008 |
| WO | 2008042005 | 4/2008 |
| WO | 2008077080 | 6/2008 |
| WO | 2008093313 | 8/2008 |
| WO | 2008103151 | 8/2008 |
| WO | 2008121294 A1 | 10/2008 |
| WO | 2008147644 | 12/2008 |
| WO | 2009036343 | 3/2009 |
| WO | 2010000047 | 1/2010 |
| WO | 2010141409 | 12/2010 |
| WO | 2010141673 | 12/2010 |
| WO | 2014116889 A1 | 7/2014 |
| WO | 2016110720 A1 | 7/2016 |
| WO | 2016186905 A1 | 11/2016 |
| WO | 2018024101 A1 | 2/2018 |

\* cited by examiner

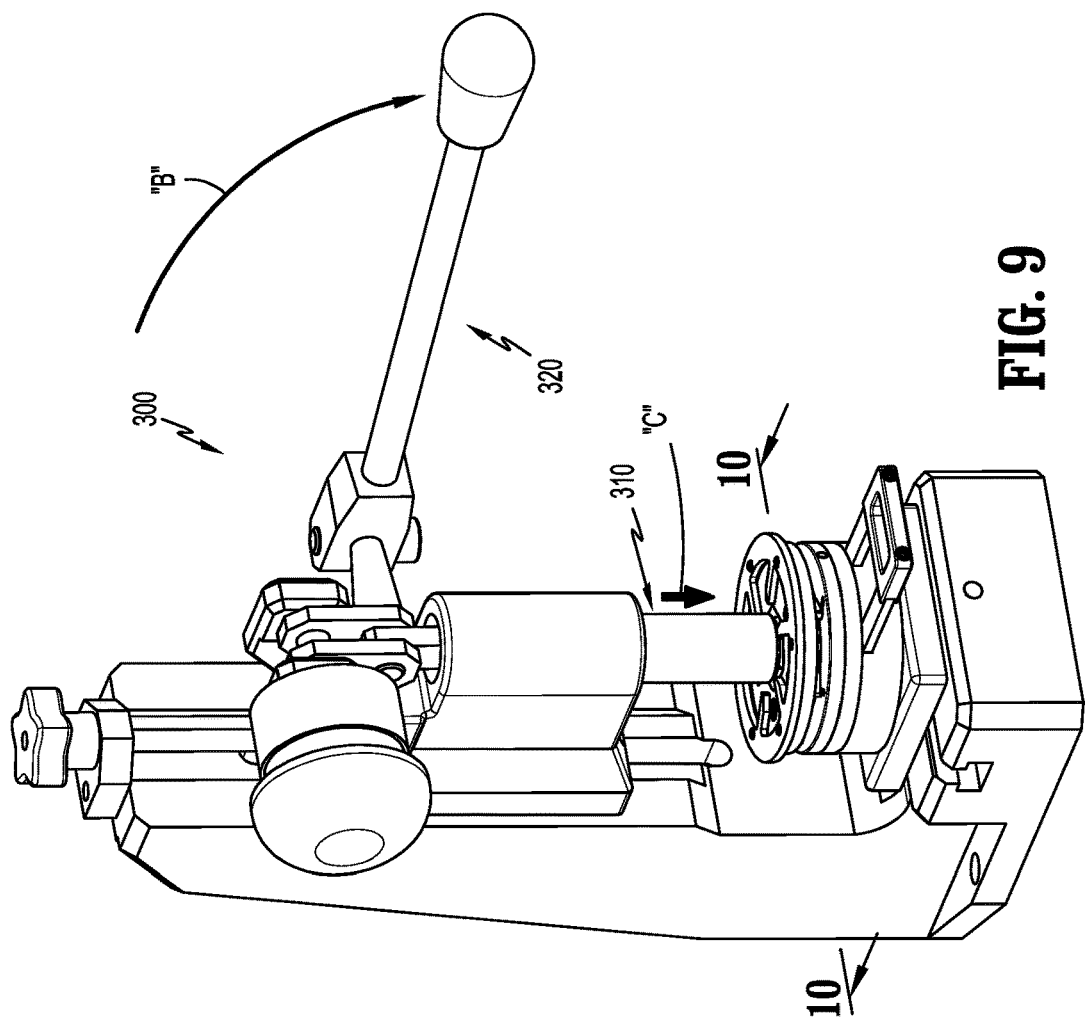
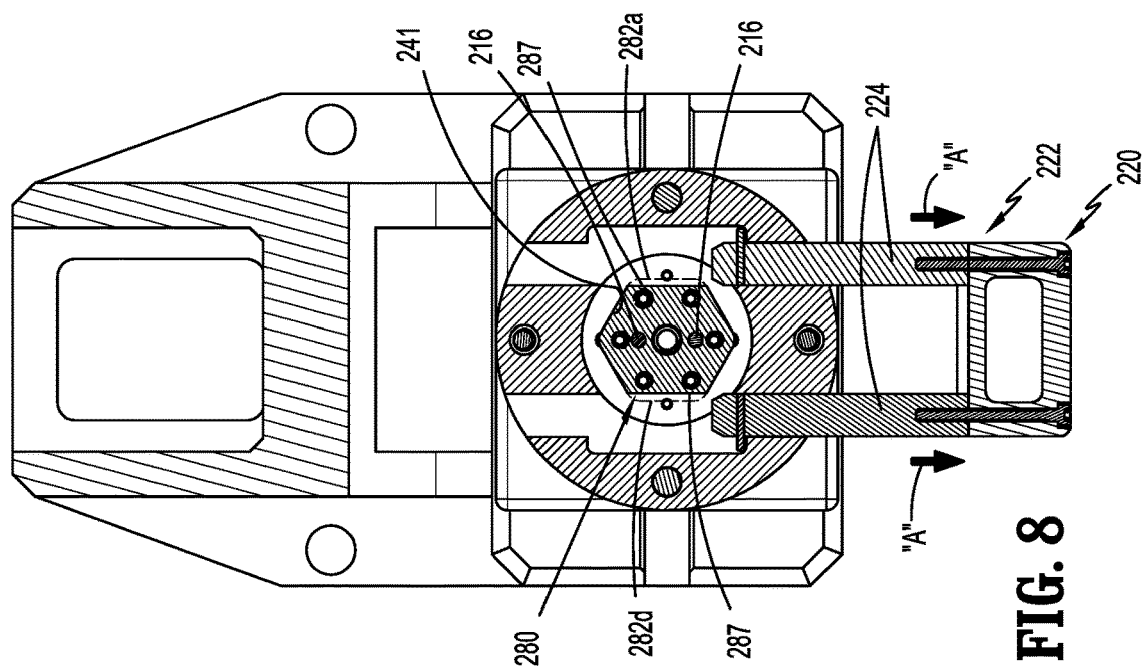
FIG. 9
FIG. 8

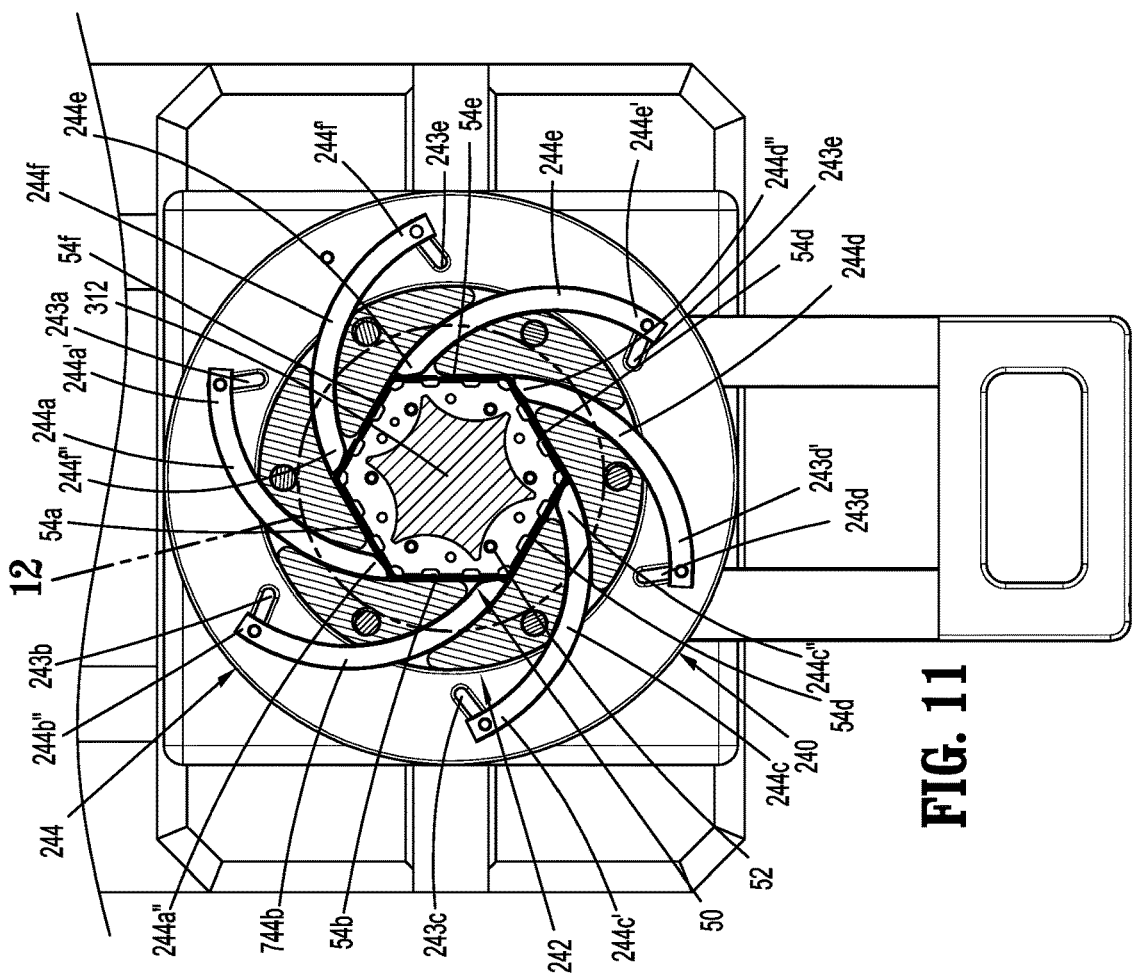
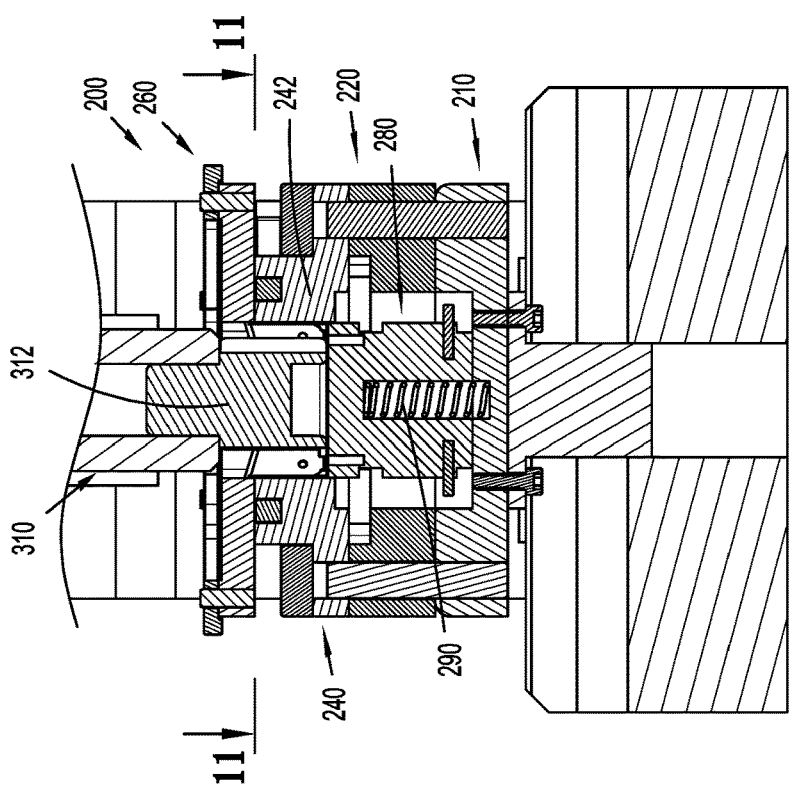
FIG. 11
FIG. 10

FIXTURE DEVICE FOR FOLDING A SEAL MEMBER

FIELD

The present disclosure relates to surgical access devices for minimally invasive surgery. More particularly, the present disclosure relates to a fixture device for folding a seal member for a surgical access device.

BACKGROUND

In order to facilitate minimally invasive surgery, a working space is created at the desired surgical site. An insufflation fluid, typically $CO_2$, is introduced into the abdomen of the patient to create an inflated state called a pneumoperitoneum. Access assemblies are utilized to allow the introduction of surgical instrumentation and endoscopes (or other visualization tools). These access assemblies maintain the pressure for the pneumoperitoneum, as they have one or more seals that adapt to the surgical instrumentation. Typically, a "zero-seal" in the access assembly seals the access assembly in the absence of a surgical instrument in the access assembly, and an instrument seal seals around a surgical instrument that has been inserted through the access assembly.

The instrument seal includes a seal member that may include a support base and a plurality of stacked petals. The petals may be independently formed and secured to the support base, or the petals may be integrally formed with the support base. The integrally formed seal member is typically formed as a flat sheet with the petals having to be folded relative to the base. To minimize leaking once formed, the petals of the seal member may be interwoven. If the petals are folded without interweaving, the durability of the seal member may be compromised and more likely to leak if torn.

Folding the petals by hand is a long and tedious process and may result in defective folding. Therefore, it would be beneficial to have a fixation device for assisting in folding the petals of the seal member.

SUMMARY

A fixation device for folding a seal member is provided. The fixation device includes a frame having a horizontal portion and an upright portion, a press assembly secured to the upright portion of the frame, and a nest assembly secured to the horizontal portion of the frame. The press assembly includes a handle assembly and an anvil assembly operably connected to the handle assembly. The nest assembly includes a clamping assembly, a folding assembly supported on the clamping assembly, a support assembly supported on the folding assembly, and a nest member. The support assembly includes a support plate and a seal clamp for securing a seal member.

In some aspects of the disclosure, the seal clamp includes a ring portion and a plurality of arm portions extending radially inward from the ring portion. The nest member may include a hexagonal shape. The nest member may be movable relative to the base between a raised position and a lowered position. A top surface of the nest assembly may define a plurality of openings for receiving retaining pins. The anvil assembly may include an anvil member configured for selective engagement with the seal member supported on the support assembly.

In certain aspects, the folding assembly includes an activation ring, a guide member, and a plurality of arm members supported on the activation ring. The guide member may define a plurality of channels configured to slidably retain the plurality of arm members. First ends of the arm members may be pivotally secured relative to the activation ring. Second ends of the arm members may be configured to engage flap portions of the seal member. The arm members are movable from a first position to a second position when the activation ring is rotated in a first direction. The plurality of arm members may include six arm members.

A method of folding a seal member using a fixation device is also provided. The method includes loading a seal member on a nest assembly of the fixation device, advancing an anvil member into engagement with a support portion of the seal member to cause folding of flap portions of the seal member relative to the support portion of the seal member, retracting the anvil member away from the seal member, activating a folding assembly to continue the folding and interweaving of the flap portions of the seal member, and advancing the anvil member into engagement with the flap portions to flatten the flap portions.

In certain aspects of the disclosure, loading the seal member on the nest assembly includes placing the seal member on a support plate of a support assembly and securing a seal clamp to the support plate. Securing the seal clamp to the support plate may include aligning arm portions of the seal clamp with sections of the flap portions of the seal member. The method may further include advancing of the anvil member into engagement with the support portion of the seal assembly causing the flap portions of the seal member to interweave. Advancing the anvil member into engagement with the support portion may include lowering a nest member of the nest assembly to a lowered position. The method may further include clamping the nest member in the lowered position.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspects given below, serve to explain the principles of the disclosure, wherein:

FIG. 8 is a top cross-sectional view of the nest assembly shown in FIG. 7 taken along line 8-8 in FIG. 7, with a clamp member of the clamp assembly in a retracted position;

FIG. 9 is a perspective view of the fixture device shown in FIG. 1, with a press assembly in an activated position;

FIG. 10 is a front cross-sectional view of the nest assembly shown in FIG. 9 taken along section line 10-10 in FIG. 9;

FIG. 11 is a top cross-sectional view of the nest assembly shown in FIG. 10 taken along section line 11-11 in FIG. 10;

DETAILED DESCRIPTION

Figure 1:
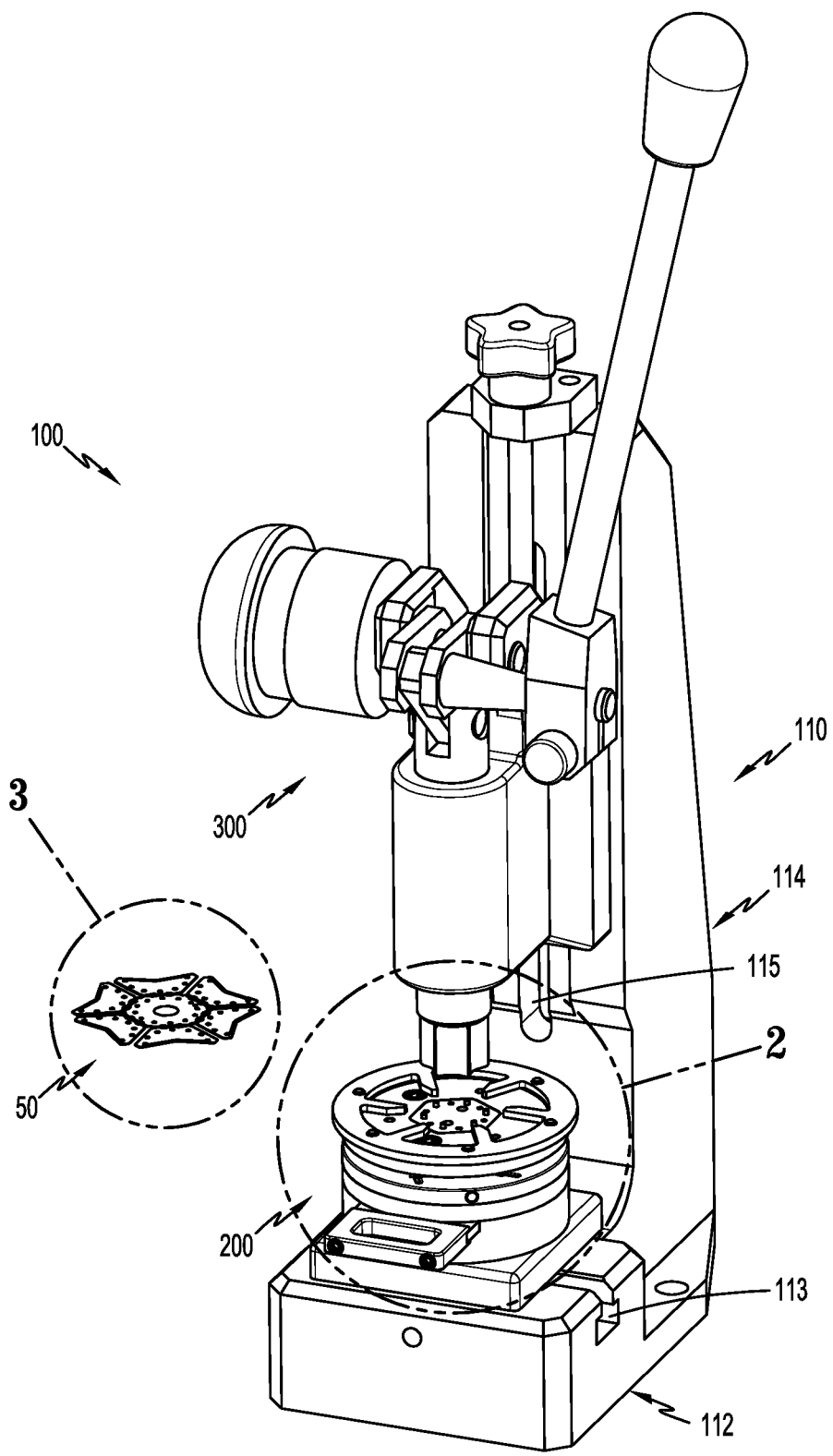
FIG. 1 is a perspective view of a fixture device for folding a seal member according to an aspect of the disclosure and a seal member.

Particular aspects of the disclosure are described hereinbelow with reference to the accompanying drawings; however, it is to be understood that the disclosed devices are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. Like reference numerals refer to similar or identical elements throughout the description of the figures.

As used herein, the term "distal" refers to that portion of the instrument, or component thereof which is farther from the user while the term "proximal" refers to that portion of the instrument or component thereof which is closer to the user. As used herein, the term "about" means that the numerical value is approximate and small variations would not significantly affect the practice of the disclosed aspects of the disclosure. Where a numerical limitation is used, unless indicated otherwise by the context, "about" means the numerical value can vary by ±10% and remain within the scope of the disclosure.

FIG. 1 illustrates a device for folding and securing a seal member shown generally as fixation device 100. The fixation device 100 includes a frame 110, a nest assembly 200 operably secured to the frame 110, and a press assembly 300 secured to the frame 110.

The frame 110 includes a base or horizontal portion 112 and a support or upright portion 114. The horizontal portion 112 of the frame 110 supports the nest assembly 200, and the upright portion 114 of the frame 110 supports the press assembly 300. The horizontal portion 112 of the frame 110 is configured to releasably and adjustably receive the nest assembly 200, and the upright portion 114 of the frame 110 is configured to releasably and adjustably receive the press assembly 300. More particularly, the base portion 112 of the frame 110 defines a channel 113 for receiving the nest assembly 200 and the upright portion 114 of the frame 110 includes a channel 115 for receiving the press assembly 300.

Figure 2:
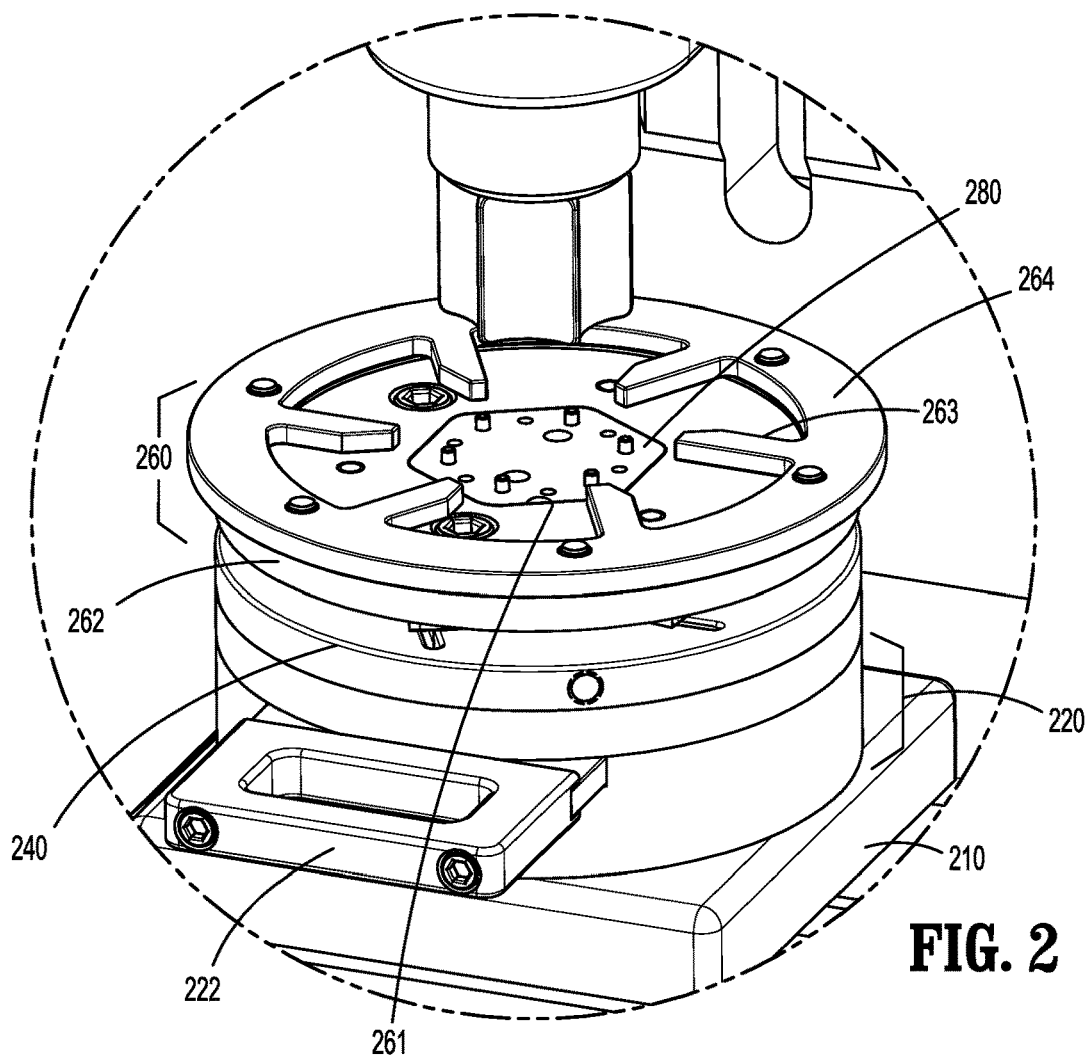
FIG. 2 is an enlarged view of the indicated area of detail shown in FIG. 1.

FIG. 2 illustrates the nest assembly 200 including a base 210, a clamp assembly 220 supported on the base 210, a folding assembly 240 supported on the clamp assembly 220, a support assembly 260 supported on the folding assembly 240, and a nest member 280 operably disposed relative to the base 210, the clamp assembly 220, the folding assembly 240, and the support assembly 260. The clamp assembly 220 is configured to selectively engage the nest member 280 to permit movement of the nest member 280 relative to the base 210, the folding assembly 240 is configured to facilitate folding of the seal member 50 (FIG. 3), the support assembly 260 retains a portion of the seal member 50 during the folding process to facilitate interweaving of flap portions 54a-f of the seal member 50, and the nest member 280 supports the seal member 50 during the folding process.

Figure 3:
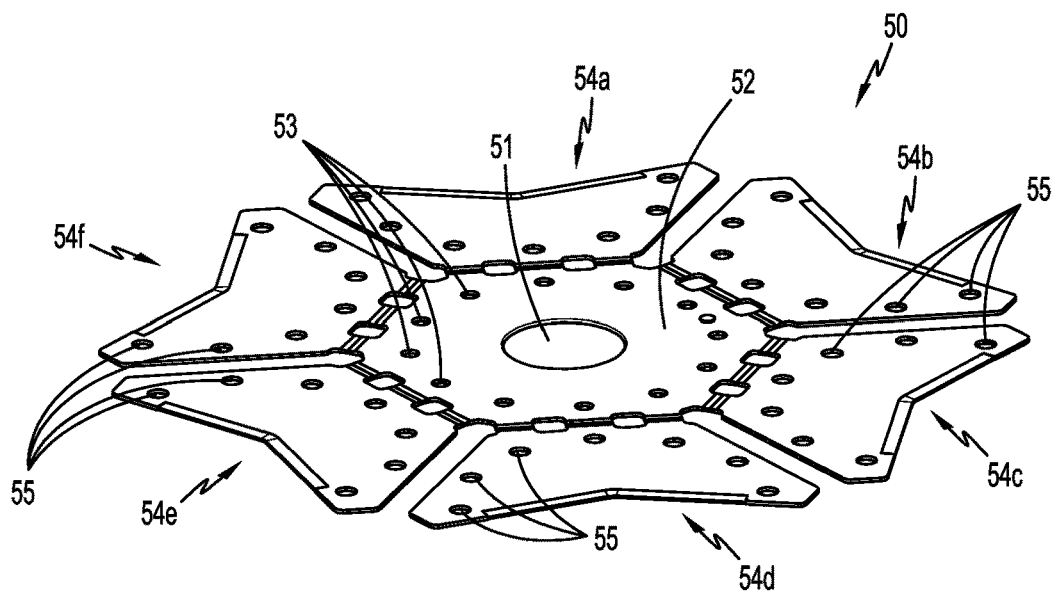
FIG. 3 is an enlarged view of the indicated area of detail shown in FIG. 1.
Figure 19:
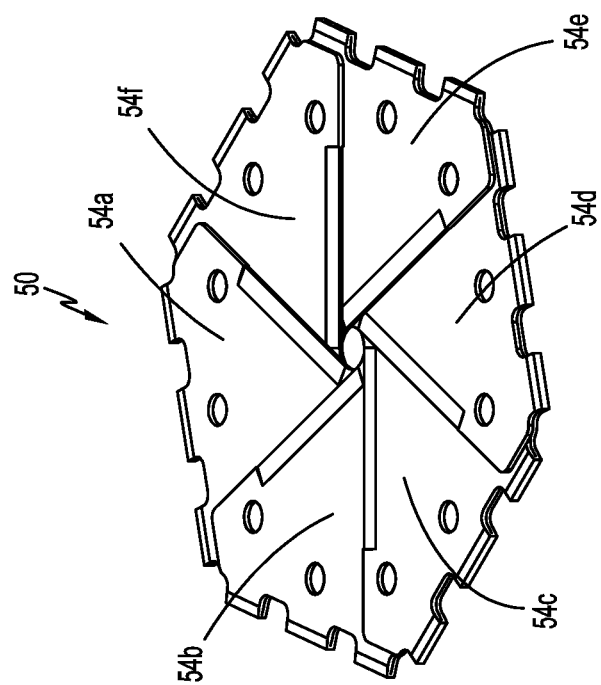
FIG. 19 is a perspective view of the seal member shown in FIG. 3, in a folded configuration.
Figure 20:
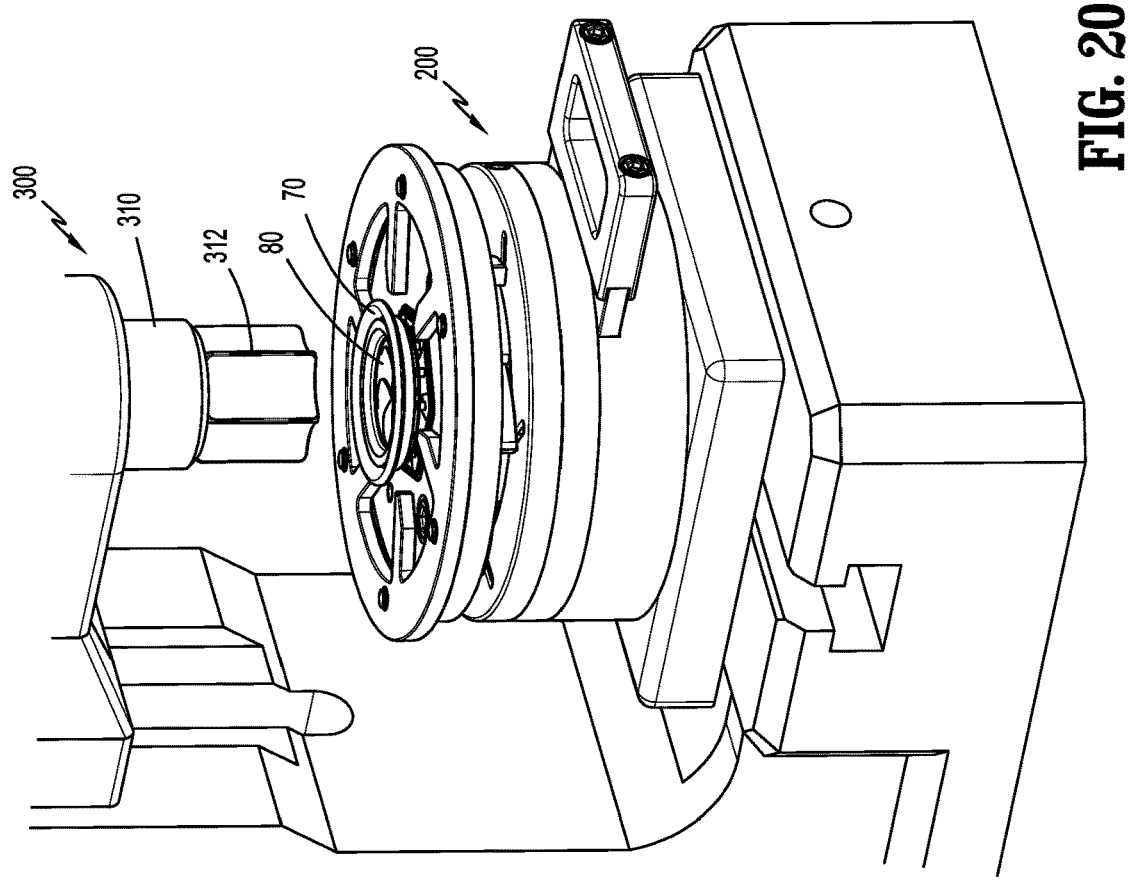
FIG. 20 is a side perspective view of the fixture device shown in FIG. 7, with an upper retaining member of a retainer assembly and a guard assembly positioned adjacent the folded seal member shown in FIG. 19.

FIG. 3 illustrates the seal member 50 configured to be folded and secured to an upper retaining member 70 and a guard assembly 80 using the fixation device 100 (see FIG. 20). The seal member 50 includes a support portion 52 and the first, second, third, fourth, fifth, and sixth flap portions 54a-f integrally formed with the support portion 52. The support portion 52 defines a central opening 51 and a plurality of openings 53 radially spaced about the central opening 51. The flap portions 54 are moveable from a flat configuration (FIG. 3) to a folded configuration (FIG. 19). Each flap portion 54a-f of the plurality of flap portions 54 defines a plurality of openings 55 about a perimeter of each of the flap portions 54a-f. The plurality of openings 55 of the flap portions 54a-f align with the plurality of openings 53 of the support portion 52 when the seal member 50 is in the folded configuration.

Figure 4:
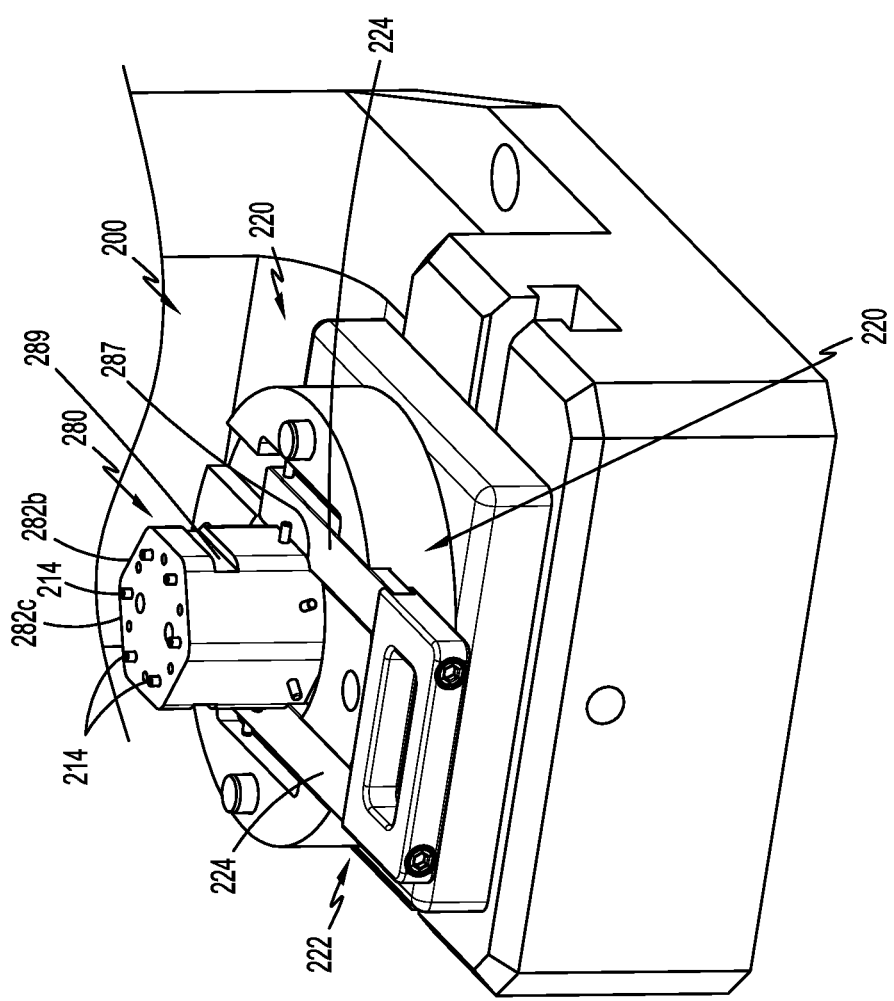
FIG. 4 is a perspective view of a base, a clamping assembly, and a nest member of a nest assembly of the fixation device shown in FIG. 1.
Figure 13:
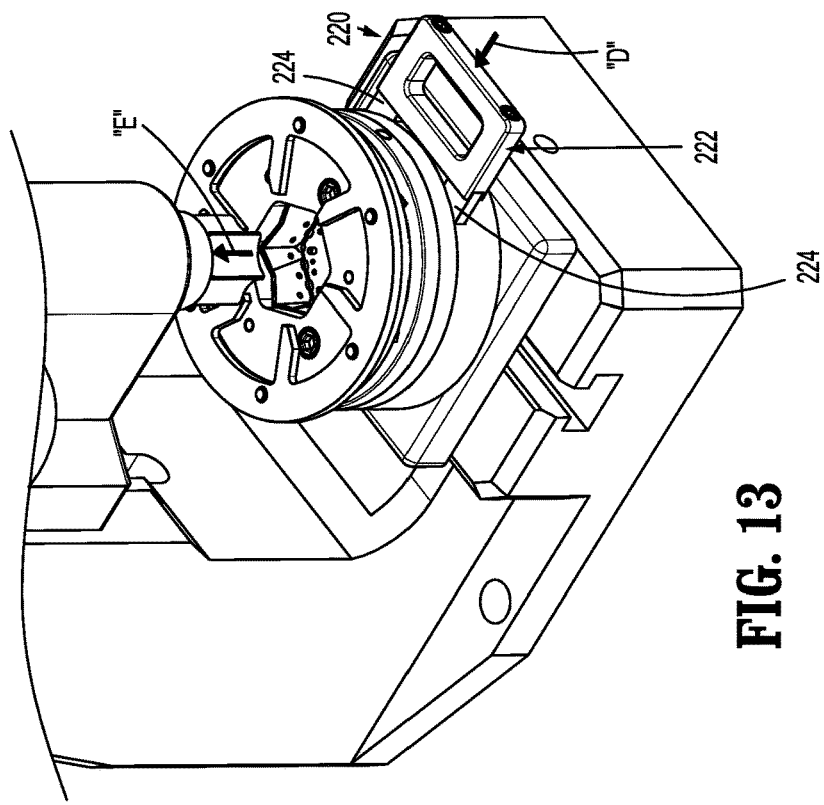
FIG. 13 is a side perspective view of the nest assembly shown in FIGS. 9-11, with the clamp assembly in a locked position and an anvil assembly of the press assembly in retracted position.

FIG. 4 illustrates the nest assembly 200 with the folding assembly 240 (FIG. 2) and the support assembly 260 removed from the base 210 and the clamp assembly 220 to expose the nest member 280. The clamp assembly 220 is configured to maintain the nest member 280 in either a first or raised position (FIG. 4) or a second or lowered position (FIG. 13).

Figure 5:
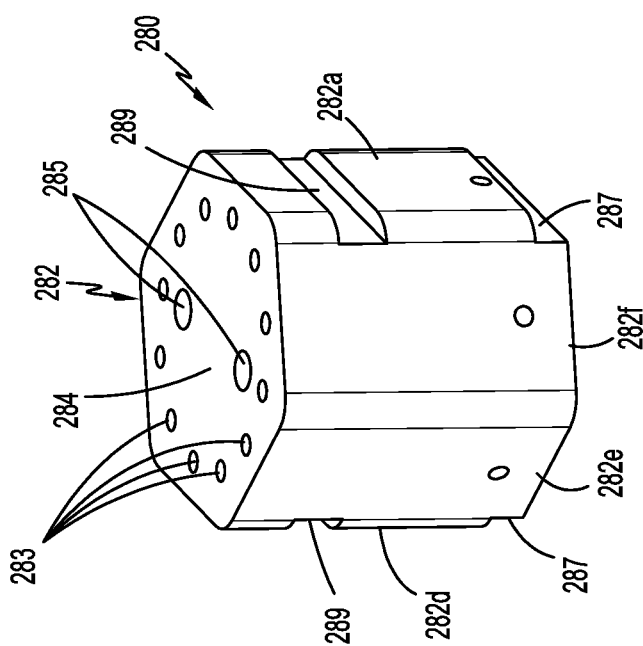
FIG. 5 is a perspective view of the nest member shown in FIG. 4.

FIG. 5 illustrates the nest member 280 including a body 282 having a hexagonal configuration corresponding to the support portion 52 (FIG. 3) of the seal member 50. A top surface 284 of the body 282 of the nest member 280 defines a plurality of openings 283 corresponding to the plurality of openings 53 in the support portion 52 of the seal member 50. The plurality of openings 283 is configured to receive alignment pins 214 (FIG. 6) for maintaining the seal member 50 relative to the nest member 280. The top surface 284 of the body 282 further defines a pair of openings 285 formed along a midline of the nest member 280. The openings 285 receive positioning pins 216 (FIG. 8) for restricting the nest member 280 from lateral movement relative to the base 210 while permitting raising and lowering of the nest member 280 during a folding process.

The body 282 of the nest member 280 includes six sides 282a-f. Opposed sides 282a, 282d each define a first slot 287 and a second slot 289. The first slots 287 in the body 282 of the nest member 280 are configured to releasably receive legs 224 (FIG. 4) of a clamp member 222 of the clamp assembly 220 to maintain the nest member 280 in a first or raised position relative to the base 210, and the second slots 289 in the opposed sides 282a, 282d of the body 282 of the nest member 280 are configured to releasably receive the legs 222 of the clamp member 222 of the clamp assembly 220 to maintain the nest member 280 in a second or lowered position relative to the base 210.

Figure 7:
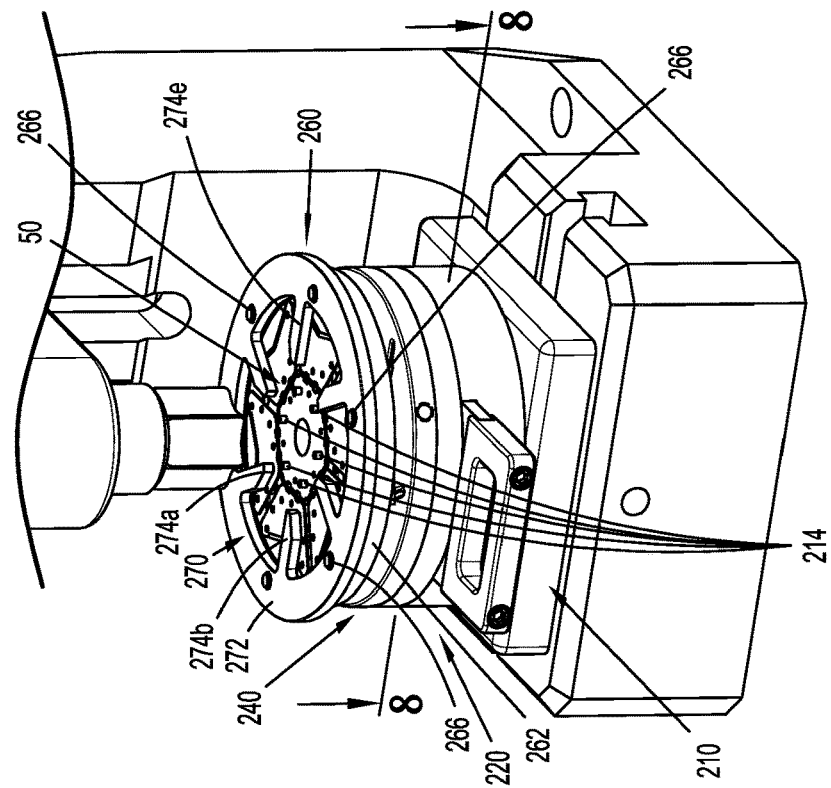
FIG. 7 is the perspective view of the nest assembly shown in FIG. 6, with the seal clamp of the support assembly secured to the support plate.
Figure 6:
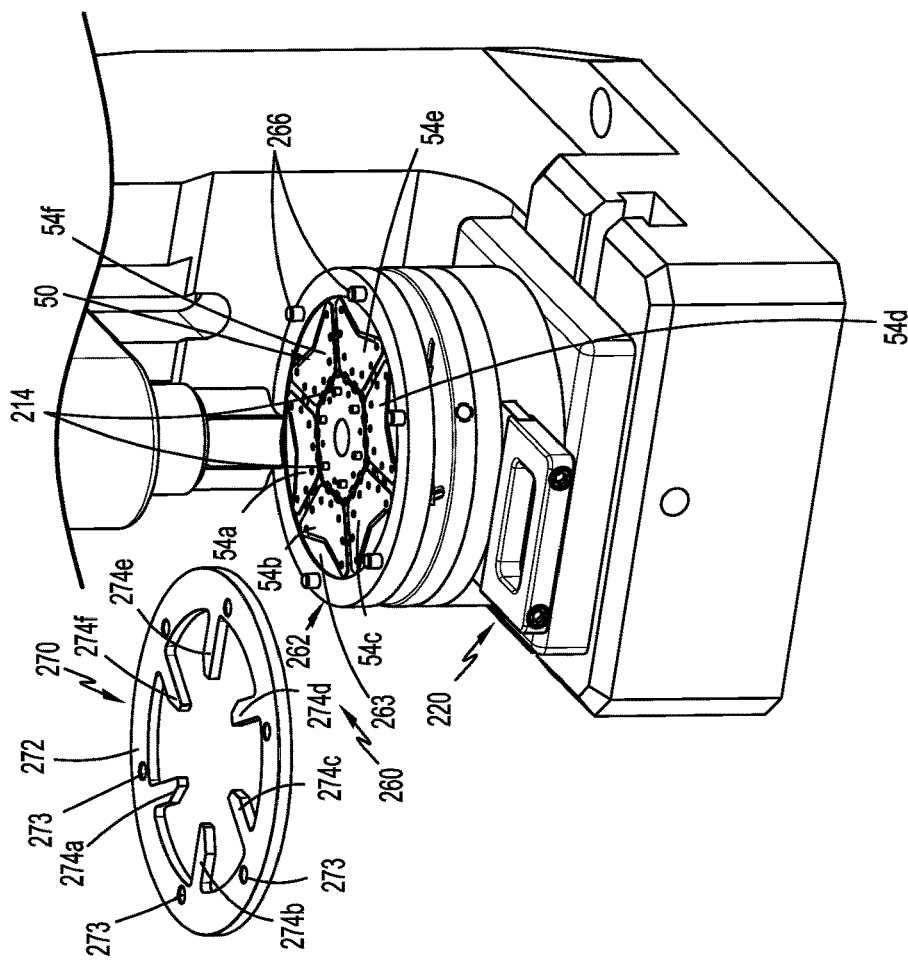
FIG. 6 is a perspective view of the nest assembly shown in FIG. 4, with a seal clamp of a support assembly separated from the support plate, and including the seal member shown in FIG. 3.

FIGS. 6 and 7 illustrate the nest assembly 200 as the seal member 50 is loaded onto the support assembly 260. The support assembly 260 includes a support plate 262 and a seal clamp 270 releasably securable to the support plate 262 to secure the seal member 50 relative to the support plate 262. The support plate 262 defines a central hexagonal opening 261 (FIG. 2) configured to receive the nest member 280 therethrough. A rim 264 (FIG. 2) extends about an outer surface of the support plate 262. The rim 264 creates a recess 263 (FIG. 3) for accommodating the flap portions 54a-f (FIG. 2) of the seal member 50 when the seal member 50 is loaded on the support plate 262. A plurality of posts 266 extend from the rim 264 of the support plate 262 and is configured to facilitate attachment of the seal clamp 270 to the support plate 262.

The seal member 50 is loaded on the support plate 262 when the nest member 280 is supported by the clamp member 222 of the clamp assembly 220 in the raised position. In this manner, the top surface 284 of the nest member 280 is flush with the support plate 262, thereby facilitating loading of the seal member 50 in its flat configuration on the nest assembly 200. More particularly, the support portion 52 of the seal member 50 is positioned on the top surface 284 of the nest member 280 and the flap portions 54a-f of the seal member 50 are positioned on the support plate 262 within the recess 263 created by the rim 264. The seal member 50 is aligned with the nest member 280 such that the retaining pins 214 received within the plurality of openings 283 in the nest member 280 align with the openings 53 in the seal member 50.

Once the seal member 50 is loaded on the support plate 262 and the nest member 280, the seal clamp 270 is secured to the support plate 262 to retain the flap portions 54a-f of the seal member 50 relative to the support plate 262. The seal plate 270 includes a ring portion 272 and a plurality of arm portions 274a-f extending radially inward from the ring portion 272. The ring portion 272 of the seal clamp 270 defines a plurality of openings 273 corresponding to the plurality of posts 266 extending from the rim 264 of the support plate 262 for receiving the plurality of posts 266 and securing the seal clamp 270 relative to the support plate 262. Each arm portion 274a-f of the seal clamp 270 is configured to engage a section of the flap portions 54a-f of the seal member 50 to maintain the flap portions 54a-f relative to the support plate 262 and to facilitate the folding of the flap portions 54a-f relative to the seal member 50. More particularly, the arm portions 274a-f of the seal clamp 270 are configured to interweave the respective flap portions 54a-f of the seal member 50 during the folding process.

FIG. 8 illustrates the nest member 280 being released from the clamp assembly 220. More particularly, the clamp member 222 of the clamp assembly 220 is retracted, as indicated by arrows "A", to disengage legs 224 of the clamp member 222 from the nest member 280, i.e., withdraw the legs 224 from within the first slots 287 in the opposed sides 282a, 282d of the nest member 280. Once the clamp member 222 is disengaged from the nest member 280, the nest member 280 is free to be pressed downwards, against the bias of a spring member 290 (FIG. 10), by the press assembly 300.

FIG. 9 illustrates activation of the press assembly 300 to engage an anvil assembly 310 of the press assembly 300 with the support member 52 of the seal member 50. More particularly, the press assembly 300 includes the anvil assembly 310 operably secured to a handle assembly 320. Rotational movement of the handle assembly 320, as indicated by arrow "B", causes an anvil member 312 (FIG. 10) of the anvil assembly 310 to advance into engagement with the support portion 52 of the seal member 50, as indicated by arrow "C". Continued advancement of the anvil assembly 310 moves the nest member 280, including the support portion 52 of the seal member 50, relative to the support member 262 of the support assembly 260 against the bias of the spring member 290 (FIG. 10) and through a central passage 241 (FIG. 8) of a guide member 242 (FIG. 11) of the folding assembly 240.

As the nest member 280 is moved relative to the support assembly 260, the flap portions 54a-f of the seal member 50, of which a section of the flap portions 54a-f are retained in place by arm portions 274a-f of the seal clamp 270 of the support assembly 260, are folded relative to the support portion 52 of the seal member 50.

Figure 12:
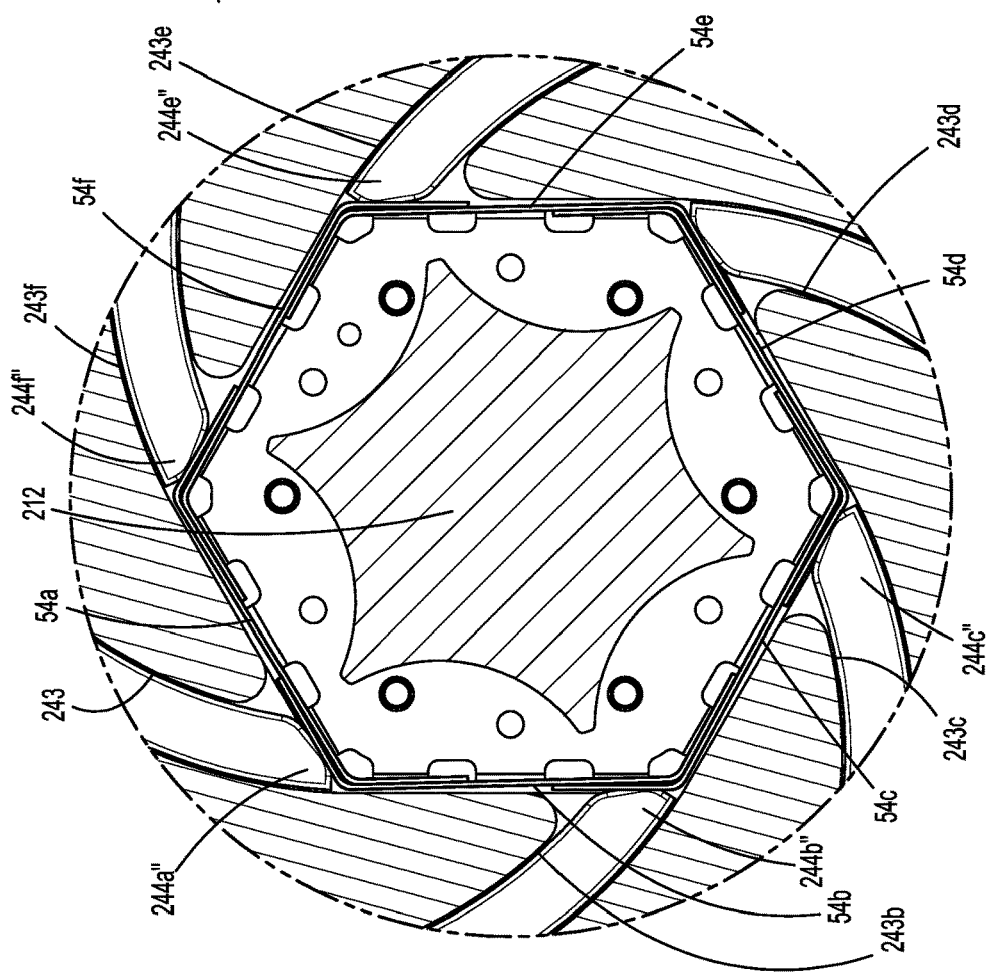
FIG. 12 is an enlarged view of the indicated area of detail shown in FIG. 11.

As the flap portions 54a-f of the seal member 50 are folded relative to the support portion 52 of the seal member 50, the engagement of the sections of the flap portions 54a-f by the respective arm portions 274a-f of the seal clamp 270 cause the flap portions 54a-f to overlap with each other in an alternating or interwoven fashion (see FIG. 12). In this manner, a first section of the first flap portion 54a overlaps a second section of sixth flap portion 54f, a first section of the second flap portion 54b overlaps a second section of the first flap portion 54a, a first section of the third flap portion 54c overlaps a second section of the second flap portion 54b, a first section of the fourth flap portion 54d overlaps a second section of the third flap portion 54c, a first section of the fifth flap portion 54e overlaps a second section of the fourth flap portion 54d, and a first section of the sixth flap portion 54f overlaps a second section of the fifth flap portion 54e.

FIGS. 10-12 illustrate the nest member 280 of the nest assembly 200 in a fully-depressed position relative to the base 210. In this position, the flap portions 54a-f of the seal member 50 are in a partially folded configuration extending perpendicular to the support portion 52 of the seal member 50 and along the central passage 241 of the guide member 242 of the folding assembly 240. As noted above, the flap portions 54a-f of the seal member 50 are also disposed in the interwoven fashion (FIG. 12).

FIG. 11 illustrates the folding assembly 240 including the guide member 242 and an activation ring 244 disposed about and rotatable relative to the guide member 244. The guide member 242 defines first, second, third, fourth, fifth, and sixth channels 243a-f aligned with the respective first, second, third, fourth, fifth, and sixth flap portions 54a-f of the seal member 50. Each of the first, second, third, fourth, fifth and sixth channels 243a-f receives a respective first, second, third, fourth, fifth, and sixth arm member 244a-f. First ends 244a'-f' of the first, second, third, fourth, fifth, and sixth arm member 244a-f, respectively, are pivotally secured within respective cam slots 243a-f formed in the activation ring 244. Second ends 244a"-f" of the arm members 244a-f are configured to align with the flap portions 54a-f, respectively, of the seal member 50.

Although the second ends 244a"-f" of the respective arm members 244a-f are aligned with the respective flap portions 54a-f of the seal member 50, the second ends 244a"-f" engage the overlapping section of the adjacent flap portions 54b-a. More particularly, the second end 244a" of the first arm member 244a engages the second flap portion 54b, the second end 244b" of the second arm member 244b engages the third flap portion 54c, the second end 244c" of the third arm member 244c engages the fourth flap portion 54d, the second end 244d" of the fourth arm member 244d engages the fifth flap portion 54e, the second end 244e" of the fifth arm member 244e engages the sixth flap portion 54f, and the second end 244f" of the sixth arm member 244f engages the first flap portion 54a.

FIG. 13 illustrates the clamp member 222 of the clamp assembly 220 being advanced, as indicated by arrow "D", into engagement with the nest member 280 to lock the nest member 280 relative to the base 210. More particularly, the legs 224 of the clamp member 222 are received within the second slots 289 (FIG. 5) in the opposed sides 282a, 282d of the nest member 280 to retain the nest member 280 in the lowered position. Once the nest member 280 is locked in the lowered position, the anvil member 312 is retracted from engagement with the support portion 52 of the seal member 50, as indicated by arrow "E" to permit operation of the folding assembly 260.

Figure 14:
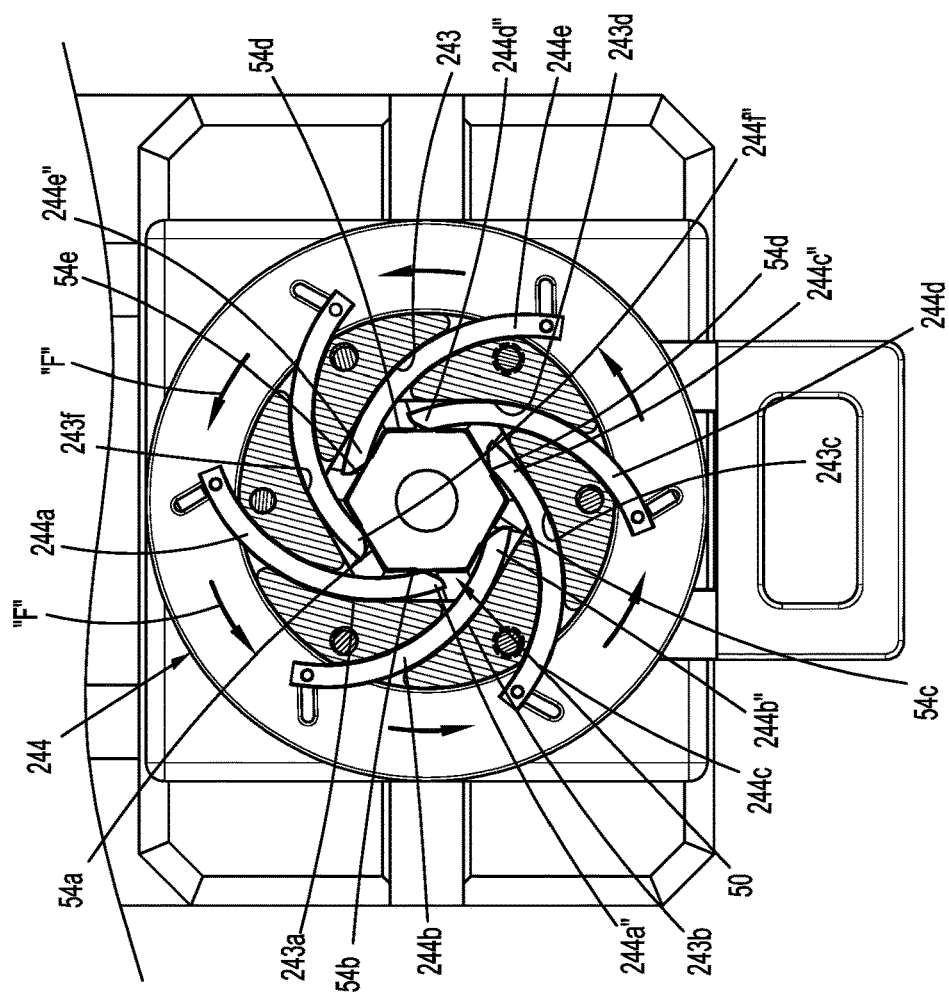
FIG. 14 is the top cross-sectional view shown in FIG. 11, with the clamp assembly in a locked position and an activation ring of a folding assembly in an activated position.

FIG. 14 illustrates rotation of the activation ring 244 in a counterclockwise direction, as indicated by arrows "F". Rotation of the activation ring 244 advances the first, second, third, fourth, fifth, and sixth arm members 244a-f of the folding assembly 240 through the respective first, second, third, fourth, fifth, and sixth channels 243a-f of the guide member 242. As the arm members 244a-f advance through the respective channels 243a-f, the second ends 244a"-f" of the arm members 244a-f move the flap portions 54a-f of the seal member 50 radially inward while maintaining the interwoven configuration of the flap portions 54a-f.

Figure 15:
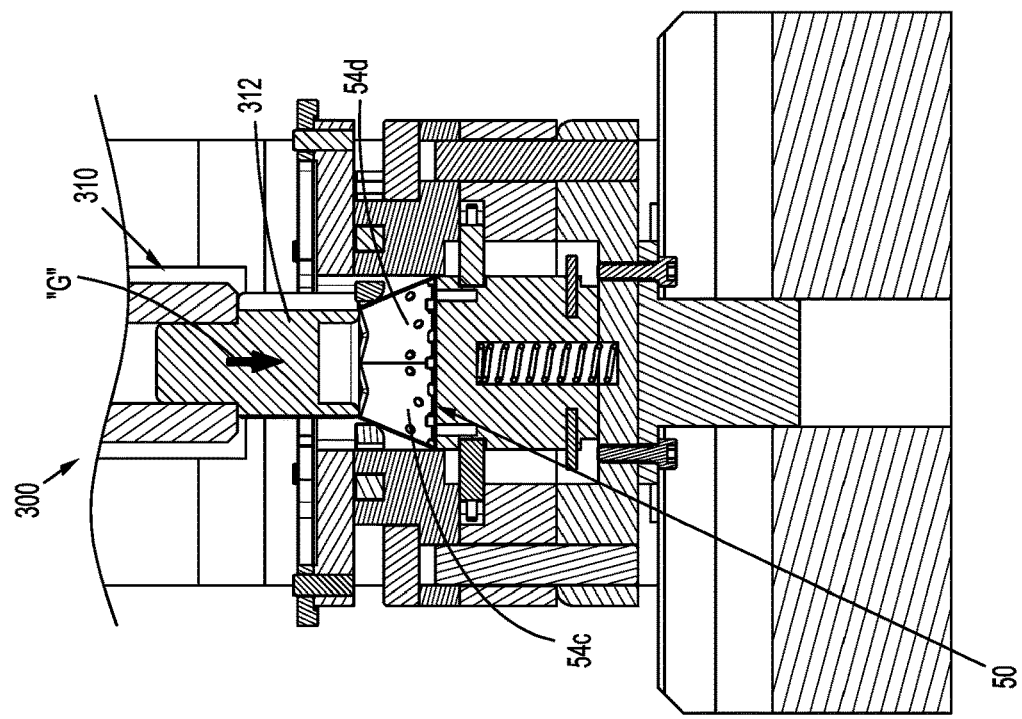
FIG. 15 is the front cross-sectional view shown in FIG. 10, with the seal member in a partially folded condition and the anvil assembly in a partially advanced position.

FIG. 15 illustrates an initial advancement of the anvil member 312 of the anvil assembly 310 of the press assembly 300 into engagement with the partially folded and interwoven flap portions 54a-f of the seal member 50, as indicated by arrow "G".

Figure 17:
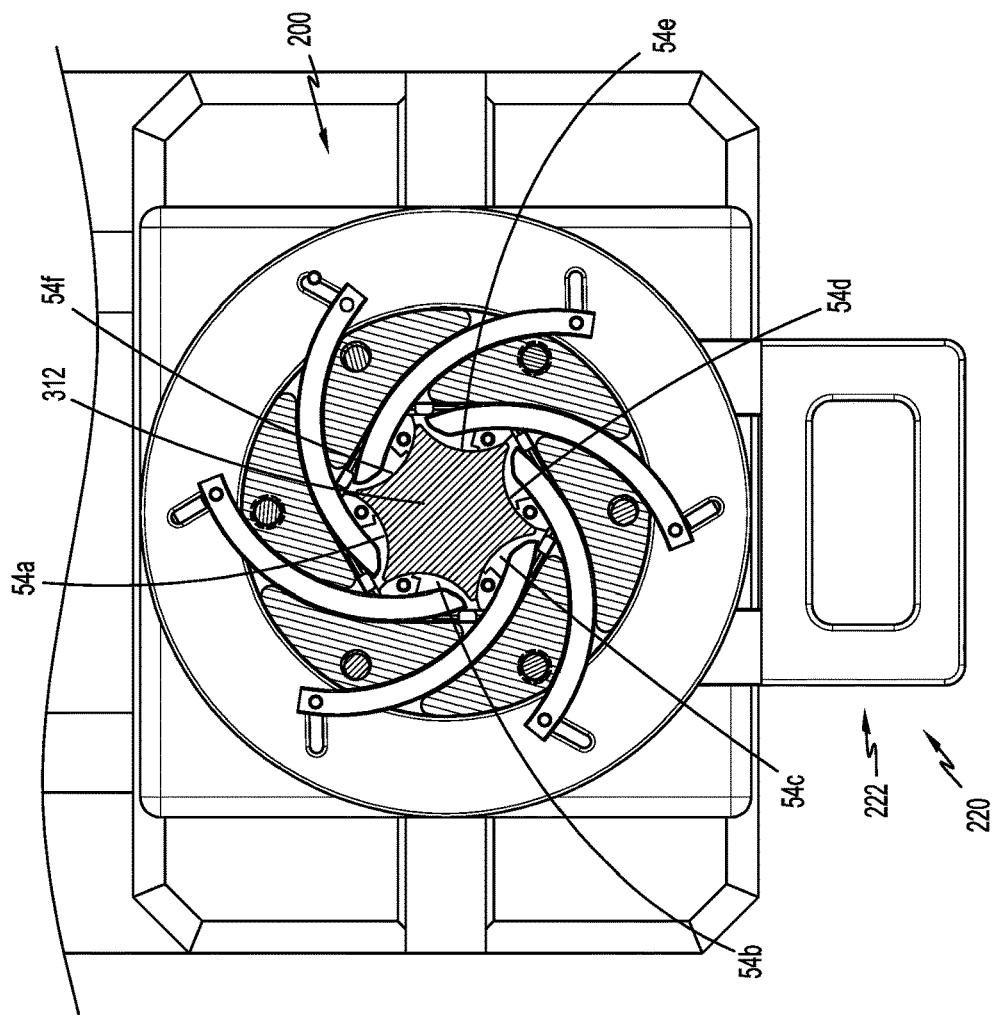
FIG. 17 is the top cross-sectional view shown in FIG. 11 with the seal member in the folded configuration and the anvil assembly in the fully advanced position.
Figure 16:
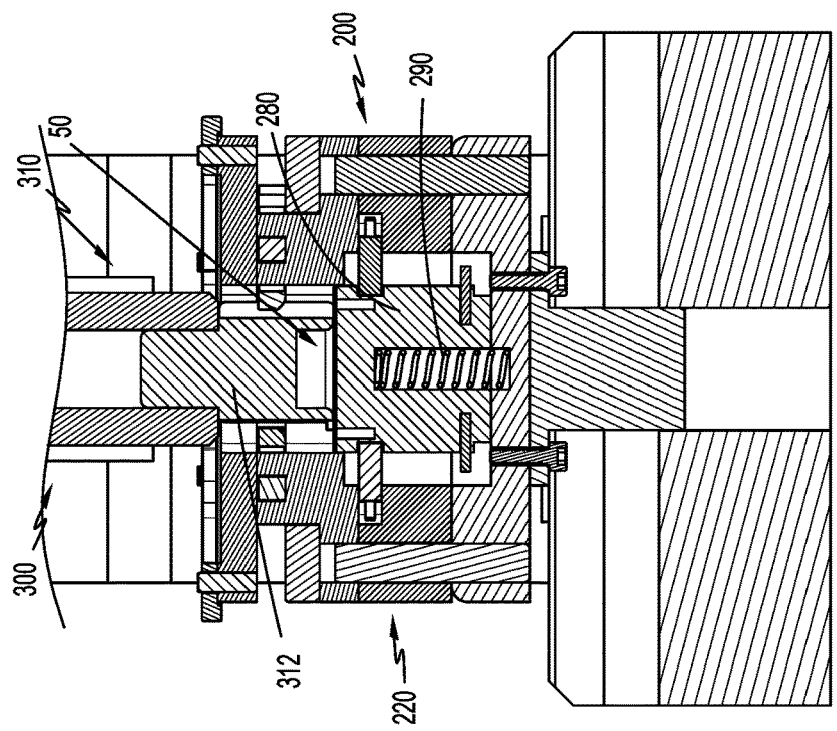
FIG. 16 is the front cross-sectional view shown in FIG. 10, with the seal member in a folded configuration and the anvil assembly in a fully advanced position.

FIGS. 16 and 17 illustrate the anvil member 312 of the anvil assembly 310 of the press assembly 300 after being fully advanced relative to the nest member 280. When the anvil member 312 of the anvil assembly 310 is in the fully advanced position, the flap portions 54a-f of the seal member 50 are completely interwoven and the seal member 50 is in the folded configuration.

Figure 18:
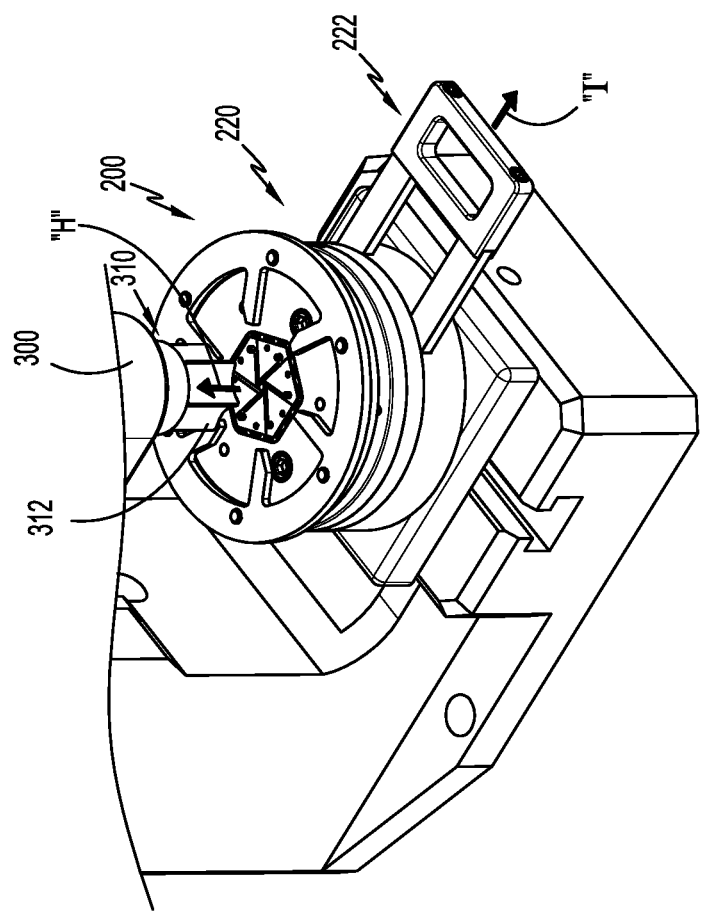
FIG. 18 is the side perspective view shown FIG. 13, with the clamp assembly in an unlocked condition and the anvil assembly in a retracted position.

FIG. 18 illustrates the return of the nest assembly 200 to its initial configuration. More particularly, the anvil member 312 of the anvil assembly 310 of the press assembly 300 is retracted relative to the nest assembly 200, as indicated by arrow "H", and the clamp member 222 of the clamp assembly 220 is withdrawn from engagement with the nest member 280, as indicated by arrow "I". In this manner, the nest member 280, including the seal member 50 in the folded configuration is returned to the raised position through the bias of the spring member 290 (FIG. 16).

FIG. 19 illustrates the seal member 50 in the folded configuration following the folding procedure with the fixation device 100.

Figure 21:
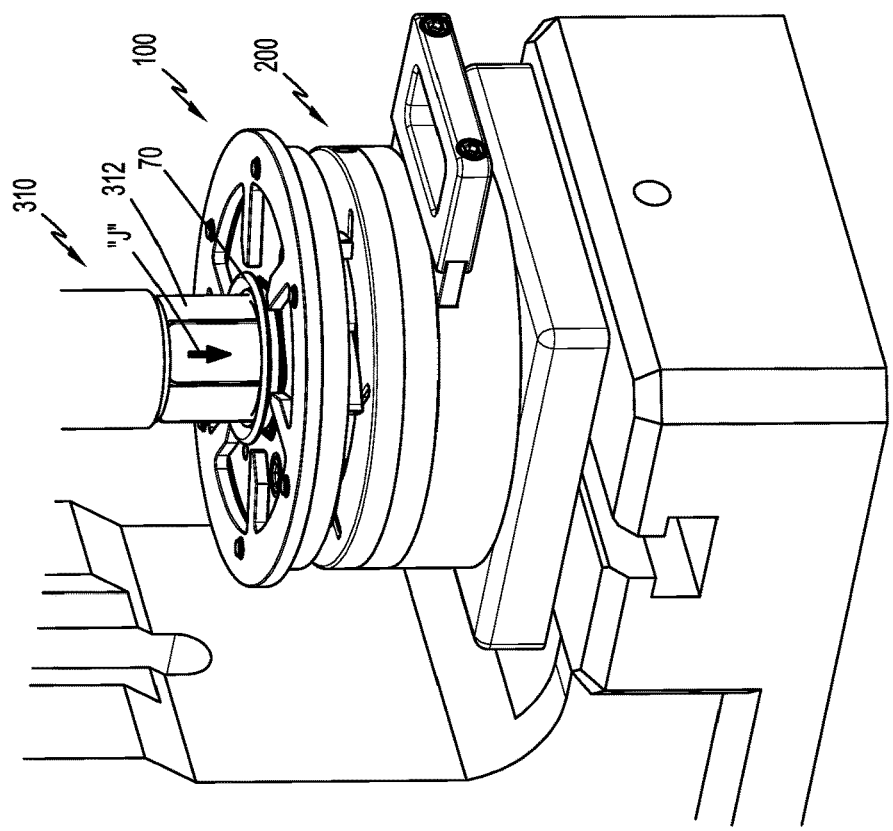
FIG. 21 is the side perspective view shown in FIG. 20, with the anvil assembly engaged with the upper retainer member.

FIGS. 20 and 21 illustrate an upper retainer member 70 and a guard assembly 80 being secured to the seal member 50. More particularly, the upper retainer member 70 of a retaining assembly and the guard assembly 80 are positioned on the seal member 50 with retaining members 72 of the upper retaining member 70 aligned with the openings 53 in the support portion 52 of the seal member 50 and the corresponding opening 55 of the flap portions 54a-f of the seal member 50. The anvil member 312 of the anvil assembly 310 of the press assembly 300 is then advanced, as indicated by arrow "J", to press fit the upper retaining member 70 and the guard assembly 80 to the seal member 50.

Figure 22:
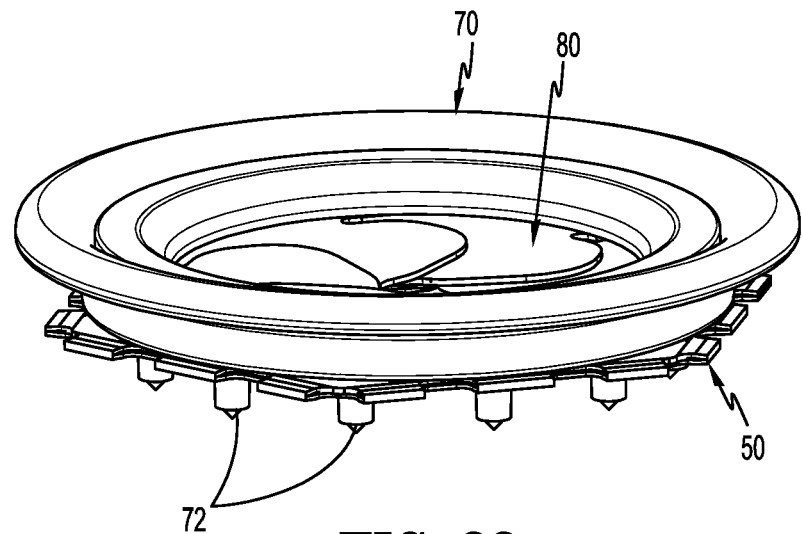
FIG. 22 is a top perspective view of an upper retainer member, a guard assembly, and the seal member shown in FIG. 3.
Figure 23:
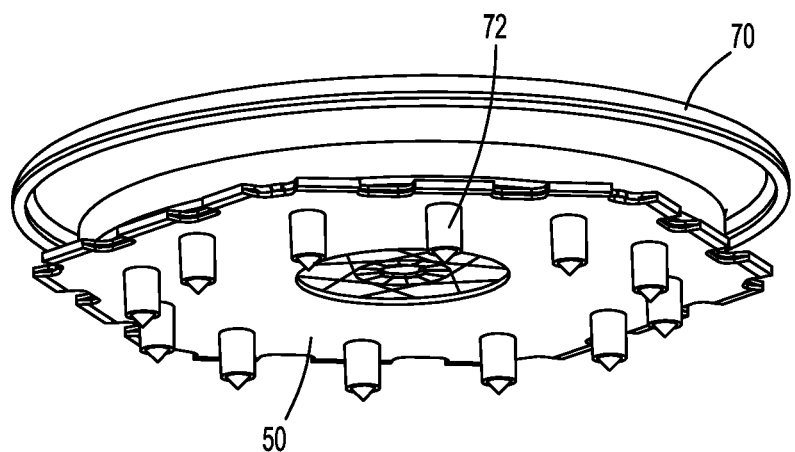
FIG. 23 is a bottom perspective view of the upper retainer member, the guard assembly, and the seal member as shown in FIG. 22.

FIGS. 22 and 23 illustrate the seal member 50, in the folded configuration, secured to the upper retainer member 70 of the retainer assembly (not shown) and the guard assembly 80. For a detailed description of an exemplary retaining assembly and guard assembly, please refer to U.S. patent application Ser. No. 16/774,206, filed Jan. 28, 2020.

It is envisioned that the folding process described above may be modified for use in an automated system. This would enable assembly of seal members at an increased rate.

While various aspects of the disclosure have been shown and described herein, it will be apparent to those skilled in the art that these aspects are provided by way of example only. Numerous variations, changes, and substitutions will now occur to those skilled in the art without departing from the disclosure. Accordingly, it is intended that the disclosure be limited only by the spirit and scope of the appended claims.

What is claimed is:

1. A fixation device for folding a seal member, the fixation device comprising:
   a frame including a horizontal portion and an upright portion;
   a press assembly secured to the upright portion of the frame, the press assembly including a handle assembly and an anvil assembly operably connected to the handle assembly; and
   a nest assembly secured to the horizontal portion of the frame, the nest assembly including a clamping assembly, a folding assembly supported on the clamping assembly, a support assembly supported on the folding assembly, and a nest member, wherein the support assembly includes a support plate and a seal clamp for securing a seal member.

2. The fixation device of claim 1, wherein the seal clamp includes a ring portion and a plurality of arm portions extending radially inward from the ring portion.

3. The fixation device of claim 1, wherein the nest member has a hexagonal shape.

4. The fixation device of claim 1, wherein the nest member is movable relative to the the horizontal portion between a raised position and a lowered position.

5. The fixation device of claim 1, wherein a top surface of the nest assembly defines a plurality of openings for receiving retaining pins.

6. The fixation device of claim 1, wherein the anvil assembly includes an anvil member configured for selective engagement with the seal member supported on the support assembly.

7. The fixation device of claim 1, wherein the folding assembly includes an activation ring, a guide member, and a plurality of arm members supported on the activation ring.

8. The fixation device of claim 7, wherein the guide member defines a plurality of channels configured to slidably retain the plurality of arm members.

9. The fixation device of claim 8, wherein first ends of the arm members are pivotally secured relative to the activation ring.

10. The fixation device of claim 9, wherein second ends of the arm members are configured to engage flap portions of the seal member.

11. The fixation device of claim 10, wherein the arm members are movable from a first position to a second position when the activation ring is rotated in a first direction.

12. The fixation device of claim 9, wherein the plurality of arm members includes six arm members.

13. A method of folding a seal member using a fixation device, the method comprising:
  loading a seal member on a nest assembly of the fixation device;
  advancing an anvil member into engagement with a support portion of the seal member to cause folding of flap portions of the seal member relative to the support portion of the seal member;
  retracting the anvil member away from the seal member;
  activating a folding assembly to continue the folding and interweaving of the flap portions of the seal member; and
  advancing the anvil member into engagement with the flap portions to flatten the flap portions.

14. The method of claim 13, wherein loading the seal member on the nest assembly includes placing the seal member on a support plate of a support assembly and securing a seal clamp to the support plate.

15. The method of claim 14, wherein securing the seal clamp to the support plate includes aligning arm portions of the seal clamp with sections of the flap portions of the seal member.

16. The method of claim 15, wherein advancing of the anvil member into engagement with the support portion of the seal assembly causes the flap portions of the seal member to interweave.

17. The method of claim 13, wherein advancing the anvil member into engagement with the support portion includes lowering a nest member of the nest assembly to a lowered position.

18. The method of claim 17, further including clamping the nest member in the lowered position.

* * * * *